(12) United States Patent
Wilén et al.

(10) Patent No.: US 11,292,968 B2
(45) Date of Patent: Apr. 5, 2022

(54) SULFENAMIDES AS FLAME RETARDANTS

(71) Applicant: Songwon International AG, Frauenfeld (CH)

(72) Inventors: Carl-Eric Wilén, Espoo (FI); Mélanie Aubert, Littoinen (FI); Teija Tirri, Rusko (FI); Weronika Pawelec, Liskow (PL)

(73) Assignee: Songwon International AG, Frauenfeld (CH)

( * ) Notice: Subject to any disclaimer, the term of this patent is extended or adjusted under 35 U.S.C. 154(b) by 943 days.

(21) Appl. No.: 15/035,290

(22) PCT Filed: Nov. 7, 2014

(86) PCT No.: PCT/EP2014/074009
§ 371 (c)(1),
(2) Date: May 9, 2016

(87) PCT Pub. No.: WO2015/067736
PCT Pub. Date: May 14, 2015

(65) Prior Publication Data
US 2016/0289566 A1    Oct. 6, 2016

(30) Foreign Application Priority Data
Nov. 8, 2013  (EP) ..................... 13192135

(51) Int. Cl.
| C08G 61/12 | (2006.01) |
| C07C 321/28 | (2006.01) |
| C09K 21/10 | (2006.01) |
| C07D 209/50 | (2006.01) |
| C07D 209/86 | (2006.01) |
| C07D 211/96 | (2006.01) |
| C07D 235/26 | (2006.01) |
| C07D 241/04 | (2006.01) |
| C07D 251/38 | (2006.01) |
| C07D 295/26 | (2006.01) |
| C07D 401/12 | (2006.01) |
| C08K 5/44 | (2006.01) |
| C09K 21/14 | (2006.01) |

(52) U.S. Cl.
CPC ............ *C09K 21/10* (2013.01); *C07C 321/28* (2013.01); *C07D 209/50* (2013.01); *C07D 209/86* (2013.01); *C07D 211/96* (2013.01); *C07D 235/26* (2013.01); *C07D 241/04* (2013.01); *C07D 251/38* (2013.01); *C07D 295/26* (2013.01); *C07D 401/12* (2013.01); *C08G 61/124* (2013.01); *C08K 5/44* (2013.01); *C09K 21/14* (2013.01); *C07C 2601/14* (2017.05)

(58) Field of Classification Search
CPC .......... C09K 5/44; C09K 21/10; C09K 21/14; C08G 61/124; C07D 209/50; C07D 209/86; C07D 211/96; C07D 235/26; C07D 241/04; C07D 251/38; C07D 295/26; C07D 401/12; C07C 321/28; C07C 2101/14; C08K 5/44
See application file for complete search history.

(56) References Cited

U.S. PATENT DOCUMENTS

| 3,296,340 A * | 1/1967 | Eichhorn ............... C07C 251/72 521/146 |
| 3,407,207 A * | 10/1968 | Longi .................. C07C 209/08 523/122 |
| 3,985,743 A | 10/1976 | Taylor |
| 4,100,327 A | 7/1978 | Smith et al. |
| 4,981,890 A | 1/1991 | Schleifstein |
| 5,424,344 A * | 6/1995 | Lewin .................. C08K 5/0066 524/156 |
| 2012/0178865 A1 | 7/2012 | Sun et al. |

FOREIGN PATENT DOCUMENTS

| CN | 1730525 A | 2/2006 | |
| CN | 101328290 A | 12/2008 | |
| CN | 102443213 A | 5/2012 | |
| CN | 102888029 A * | 1/2013 | ............... C08K 5/09 |
| CN | 102918096 A | 2/2013 | |
| EP | 0496119 A1 | 7/1992 | |
| EP | 2553008 B1 * | 8/2016 | .......... C08K 5/0066 |
| FR | 1391298 | 3/1965 | |
| JP | S495439 B1 | 2/1974 | |
| JP | S5276355 A | 6/1977 | |
| JP | 53124273 A | 10/1978 | |
| JP | H1180568 A | 3/1999 | |
| WO | 9900450 A1 | 1/1999 | |
| WO | 2005030852 A2 | 4/2005 | |
| WO | 2008101845 A1 | 8/2008 | |
| WO | WO-2011121001 A1 * | 10/2011 | ............... C08K 5/36 |
| WO | 2013017417 A1 | 2/2013 | |

OTHER PUBLICATIONS

J. Eichhorn, Synergism of Free Radical Initiators with Self-Extinguishing Additives in Vinyl Aromatic Polymers, Journal of Applied Polymer Science vol. 8, pp. 2497-2524 (1964). (Year: 1964).*

(Continued)

*Primary Examiner* — Bijan Ahvazi

(74) *Attorney, Agent, or Firm* — Barnes & Thornburg LLP

(57) ABSTRACT

The present invention is in the field of flame retardants and relates to use of sulfenamides as flame retardants, in particular in polymeric substrates.

17 Claims, No Drawings

(56) References Cited

OTHER PUBLICATIONS

Nobukazu Taniguchi, Copper-Catalyzed Synthesis of Sulfenamides Utilizing Diaryl Disulfides with Alkyl Amines,SYNLETT 2007, No. 12, pp. 1917-1920. (Year: 2007).*
Chinese Office Action corresponding to Chinese Application 201480068826X, dated Aug. 14, 2017.
Eichhorn, J.; Synergism of Free Radical Initiators with Self-Extinguishing Additives in Vinyl Aromatic Polymers; Journal of Applied Polymer Science, vol. 8, pp. 2497-2524, 1964.
European Search Report for EP 13 19 2135 dated Apr. 7, 2014.
Written Opinion of the International Searching Authority and International Search Report for International Patent Application No. PCT/EP2014/074009; dated Feb. 3, 2015.
JP Office Action for corresponding Japanese application, dated Sep. 10, 2020, 55 pages.
Translation of Chinese Notification of First Office Action, Chinese Application No. 2019110243591, dated Mar. 9, 2021, 18 pages.

* cited by examiner

SULFENAMIDES AS FLAME RETARDANTS

CROSS REFERENCE AND PRIORITY

This patent application is a U.S. National Phase of International Patent Application No. PCT/EP2014/074009, filed 7 Nov. 2014, which claims priority to European Patent Application No. 13192135.5, filed the disclosure of which are incorporated herein by reference in their entirety.

FIELD

Disclosed embodiments are in the field of flame retardants and relates to use of sulfenamides as flame retardants, in particular in polymeric substrates.

BACKGROUND

Flame retardant(s) are added to both synthetic and natural polymeric materials to enhance the flame retardant properties of the polymers. Both inorganic and organic compounds have been used for achieving the flame retardant properties in various types of polymers. The main types of flame retardants include halogenated hydrocarbons, phosphorous containing compounds, metallic compounds such as metal oxides and hydroxides, and melamine derivatives. Halogenated flame retardants are commonly used due to their effectiveness. Nevertheless, the use of halogenated compounds has generally become of an environmental concern.

To diminish the problems relating to halogenated flame retardants, synergists are often used in combination with halogenated flame retardants. Synergists are compounds which enhance the flame retarding properties of the other flame retardants and thus enable to use the other flame retardants in substantially reduced amounts. Synergistic compounds encompass a group of compounds known as "free radical initiators" which include organic peroxide (see e.g., U.S. Pat. No. 3,058,926), dibenzyl compounds (see e.g., U.S. Pat. Nos. 3,271,333 and 3,420,786), disulfides (see e.g., U.S. Pat. No. 3,284,544), hydrazones (see. U.S. Pat. No. 3,269,962), sulfenamides (see e.g., U.S. Pat. No. 3,296,340 and FR1391298) and azocompounds see (e.g., U.S. Pat. Nos. 4,237,179, 3,897,373, 4,486,347 and FR1425563). Such synergists are used only in combination with other flame retardants, and typically with halogenated flame retardants, and/or they may be halogenated themselves.

Non-halogenated N-hydrocarbyloxy hindered amines (also known as NOR-hindered amines) have also been proposed as alternative flame retardants. These can be used alone, e.g., in place of halogenated flame retardants, or as synergists for flame retardant applications (see e.g WO9900450). Moreover, some non-halogenated azo, hydrazine and peroxide derivatives have also be suggested for improving the flame retarding properties of some polymers (see e.g., WO2005030852 and WO2008101845).

However, there still exists a need for effective non-halogenated flame retarding compounds, which would provide an industrially and environmentally desirable alternative for the halogenated flame retardant compounds.

BRIEF DESCRIPTION

Disclosed embodiments provide non-halogenated flame retardant compounds so as to overcome the above disadvantages. This is achieved by use of compound of formula (I) as flame retarding compounds, flame retarding compositions comprising the compound of formula (I).

Disclosed embodiments are based on the surprising realization that sulfenamides provide excellent flame retarding properties to polymer substrates either if applied alone or in combination with other halogen free flame retardants. The compounds bear specific S—N core which has not been disclosed in the prior art as posses sing any flame retarding activity per se.

DETAILED DESCRIPTION

Disclosed embodiments relate to use of a compound of formula (I) as a flame retardant, the compound of formula (I) having structure

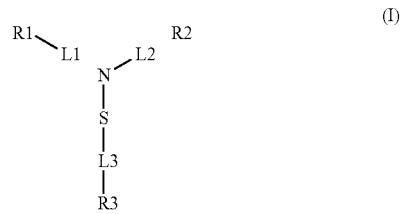

(I)

wherein

L1, L2, and L3 are each independently selected from a group consisting of a bond, $C_{1-10}$-alkylenyl, —(C=O)—, —O—(C=O)—, —(C=O)—O—, O, NH—(C=O)—, —(C=O)—NH—, NH, and NR20;

each R1 and R2 is independently selected from a group consisting of H, $S(=O)_pR3$, $C_{1-30}$-alkyl, $C_{3-7}$-cycloalkyl optionally substituted one or more times with R10, $C_{2-30}$-alkenyl, $C_{2-30}$-alkynyl, $C_{1-10}$-alkylenyl-X—$C_{1-20}$-alkyl, $C_{1-10}$-alkylenyl-X—$C_{1-7}$-cycloalkyl optionally substituted one or more times with R10, a saturated or partly unsaturated mono- or bicyclic heterocycle optionally substituted one or more times with R10, and a mono- or bicyclic aryl or heteroaryl optionally substituted one or more times with R10; or L1, L2, R1, and R2 together with the N atom they are attached to form a NR1R2 group selected from a group consisting of a saturated or partly unsaturated mono- or bicyclic heterocycle optionally substituted one or more times with R10; a mono-, bi-, tri-, tetra- or pentacyclic heteroaryl optionally substituted one or more times with R10; N=CR1'R2'; and N=S=S;

R3 is selected from a group consisting of $C_{1-30}$-alkyl, $C_{3-7}$-cycloalkyl optionally substituted one or more times with R30, $C_{2-30}$-alkenyl, $C_{2-30}$-alkynyl, NR1R2, a saturated or party unsaturated mono- or bicyclic heterocycle optionally substituted one or more times with R30, and a mono-, bi-, or tricyclic aryl or heteroaryl optionally substituted one or more times with R30;

or

L1, L3, R1, and R3 together with the N atom and the S atom they are attached to from a group selected from a mono-, bi-, or tricyclic heteroaryl optionally substituted one or more times with R40, and a saturated or partly unsaturated mono- or bicyclic heterocycle optionally substituted one or more times with R40; and R2 is as defined above;

or

L1, L2, L3, R1, R2, and R3 together with the S atom and the N atom to which they are attached to form a mono-, bi- or tricyclic heteroaryl optionally substituted one or more times with R50;

each R1' and R2' is independently R1 or R2, respectively, as defined above, or R1' and R2' form together with the C atom they are attached to a CR1'R2' group selected from a group consisting of a $C_{3-7}$-cycloalkyl optionally substituted one or more times with R10, a saturated or partly unsaturated mono- or bicyclic heterocycle optionally substituted one or more times with R10, a mono- or bicyclic aryl or heteroaryl optionally substituted one or more times with R10, X is O, S, NH, NR20, P, Si, or Se;

each R10 is independently selected from a group consisting of $NO_2$, CN, $SO_3H$, COOH, COOR20, CHO, COR20, OCOR20, O(C=O)O—(NR1"R2")—S(=O)$_p$R3, =O, =S, R20, NHCOR20, $NH_2$, NHR20, $N(R20)_2$, OH, OR20, $OSiH_3$, $OSi(R20)_3$, S(=O)$_p$R3, =N—S(=O)$_p$R3, —N=N—(R1"R2"N)—S(=O)$_p$R3, and =N—N=(R1"R2"N)S(=O)$_p$R3, wherein R1"R2"N forms a monocyclic saturated heterocycle optionally substituted with one or more R10'; provided that when R10 is O(C=O)O—(NR1"R2")—S(=O)$_p$R3, S(=O)$_p$R3, =N—S(=O)$_p$R3, —N=N(R1"R2"N)—S(=O)$_p$R3, or =N—N=(R1"R2"N)— S(=O)$_p$R3, the R3 is not substituted with NR1R2 or SNR1R2;

each R10' is independently selected from a group consisting of $NO_2$, CN, $SO_3H$, COOH, COOR20, CHO, COR20, OCOR20, =O, R20, NHCOR20, $NH_2$, NHR20, $N(R20)_2$, OH, OR20, $OSiH_3$, and $OSi(R20)_3$;

each R20 is independently selected from a group consisting of $C_{1-30}$-alkyl, $C_{2-30}$-alkenyl, $C_{2-30}$-alkynyl, aryl, $C_{1-10}$-alkylenyl-aryl, heteroaryl, and $C_{1-10}$-alkylenyl-heteroaryl, wherein the aryl or heteroaryl is optionally substituted one or more times with $C_{1-4}$-alkyl, $NO_2$, CN, $NH_2$, $NMe_2$, OH and/or OMe;

each R30 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, and S(=O)$_p$—NR1R2, provided that when R30 is NR1R2 or S(=O)$_p$—NR1R2 the NR1R2 is not substituted with O(C=O)O—(NR1"R2")—S(=O)$_p$R3, S(=O)$_p$R3, =N—S(=O)$_p$R3, —N=N—(R1"R2"N)—S(=O)$_p$R3, or =N—N=(R1"R2"N)S(=O)$_p$R3;

each R40 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, S(=O)$_p$R3 and a saturated or partly unsaturated monocyclic heterocycle optionally substituted one or more times with R10', provided that when R40 is NR1R2 or S(=O)$_p$R3 the R3 is not substituted with NR1R2 or S(=O)$_p$—NR1R2 and the NR1R2 is not substituted with O(C=O)O—(NR1"R2")—S(=O)$_p$R3, —S(=O)$_p$R3, =NS(=O)$_p$R3, —N=N—(R1"R2"N)—S(=O)$_p$R3, or =N—N=(R1"R2"N)—S(=O)$_p$R3;

each R50 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, S(=O)$_p$R3, and a saturated or partly unsaturated monocyclic heterocycle optionally substituted one or more times with R10', provided that when R50 is NR1R2 or S(=O)$_p$R3 the R3 is not substituted with NR1R2 or S(=O)$_p$—NR1R2 and the NR1R2 is not substituted with O(C=O)O—(NR1"R2")—S(=O)$_p$R3, S(=O)$_p$R3, =NS(=O)$_p$R3, —N=N—(R1"R2"N)—S(=O)$_p$R3, or =N—N=(R1"R2"N)—S(=O)$_p$R3; and each p is independently selected from the group consisting of 0, 1 and 2.

Further, disclosed embodiments relate to use of a polymer comprising one or more repeating units, wherein at least one of the repeating units comprises a sulfenamide moiety of formula (II), as a flame retardant

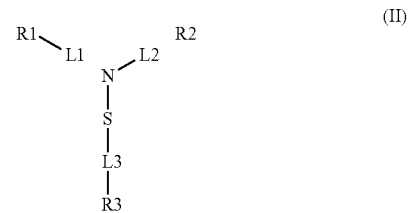

(II)

wherein the sulfenamide moiety is included in a main chain of the polymer, in a pendant group of the polymer or is part of a crosslink of the polymer and wherein L1, L2, and L3 are each independently selected from a group consisting of a bond, $C_{1-10}$-alkylenyl, —(C=O)—, —O—(C=O)—, —(C=O)—O—, O, NH—(C=O)—, —(C=O)—NH—, NH, and NR20;

each R1 and R2 is independently selected from a group consisting of H, S(=O)$_p$R3, $C_{1-30}$-alkyl, $C_{3-7}$-cycloalkyl optionally substituted one or more times with R10, $C_{2-30}$-alkenyl, $C_{2-30}$-alkynyl, $C_{1-10}$-alkylenyl-X—$C_{1-20}$-alkyl, $C_{1-10}$-alkylenyl-X—$C_{1-7}$-cycloalkyl optionally substituted one or more times with R10, a saturated or partly unsaturated mono- or bicyclic heterocycle optionally substituted one or more times with R10, and a mono- or bicyclic aryl or heteroaryl optionally substituted one or more times with R10; or L1, L2, R1, and R2 together with the N atom they are attached to form a NR1R2 group selected from a group consisting of a saturated or partly unsaturated mono- or bicyclic heterocycle optionally substituted one or more times with R10; a mono-, bi-, tri-, tetra- or pentacyclic heteroaryl optionally substituted one or more times with R10; N=CR1'R2'; and N=S=S;

R3 is selected from a group consisting of $C_{1-30}$-alkyl, $C_{3-7}$-cycloalkyl optionally substituted one or more times with R30, $C_{2-30}$-alkenyl, $C_{2-30}$-alkynyl, NR1R2, a saturated or party unsaturated mono- or bicyclic heterocycle optionally substituted one or more times with R30, and a mono-, bi-, or tricyclic aryl or heteroaryl optionally substituted one or more times with R30;

or

L1, L3, R1, and R3 together with the N atom and the S atom they are attached to from a group selected from a mono-, bi-, or tricyclic heteroaryl optionally substituted one or more times with R40, and a saturated or partly unsaturated mono- or bicyclic heterocycle optionally substituted one or more times with R40; and R2 is as defined above;

or

L1, L2, L3, R1, R2, and R3 together with the S atom and the N atom to which they are attached to form a mono-, bi- or tricyclic heteroaryl optionally substituted one or more times with R50;

each R1' and R2' is independently R1 or R2, respectively, as defined above, or R1' and R2' form together with the C atom they are attached to a CR1'R2' group selected from a group consisting of a $C_{3-7}$-cycloalkyl optionally substituted one or more times with R10, a saturated or partly unsaturated mono- or bicyclic heterocycle optionally substituted one or more times with R10, a mono- or bicyclic aryl or heteroaryl optionally substituted one or more times with R10, X is O, S, NH, NR20, P, Si, or Se;

each R10 is independently selected from a group consisting of NO$_2$, CN, SO$_3$H, COOH, COOR20, CHO, COR20, OCOR20, O(C=O)O—(NR1"R2")—S(=O)$_p$R3, =O, =S, R20, NHCOR20, NH$_2$, NHR20, N(R20)$_2$, OH, OR20, OSiH$_3$, OSi(R20)$_3$, S(=O)$_p$R3, =N—S(=O)$_p$R3, —N=N—(R1"R2"N)—S(=O)$_p$R3, and =N—N=(R1"R2"N)S(=O)$_p$R3, wherein R1"R2"N forms a monocyclic saturated heterocycle optionally substituted with one or more R10'; provided that when R10 is O(C=O)O—(NR1"R2")S(=O)$_p$R3, S(=O)$_p$R3, =N—S(=O)$_p$R3, —N=N—(R1"R2"N)—S(=O)$_p$R3, or =N—N=(R1"R2"N)— S(=O)$_p$R3, the R3 is not substituted with NR1R2 or SNR1R2;

each R10' is independently selected from a group consisting of NO$_2$, CN, SO$_3$H, COOH, COOR20, CHO, COR20, OCOR20, =O, R20, NHCOR20, NH$_2$, NHR20, N(R20)$_2$, OH, OR20, OSiH$_3$, and OSi(R20)$_3$;

each R20 is independently selected from a group consisting of C$_{1-30}$-alkyl, C$_{2-30}$-alkenyl, C$_{2-30}$-alkynyl, aryl, C$_{1-10}$-alkylenyl-aryl, heteroaryl, and C$_{1-10}$-alkylenyl-heteroaryl, wherein the aryl or heteroaryl is optionally substituted one or more times with C$_{1-4}$-alkyl, NO$_2$, CN, NH$_2$, NMe$_2$, OH and/or OMe;

each R30 is independently selected from a group consisting of NO$_2$, CN, SO$_3$H, COOH, COOR20, CHO, COR20, OCOR20, =O, R20, OH, OR20, OSiH$_3$, OSi(R20)$_3$, NHCOR20, NR1R2, and S(=O)$_p$—NR1R2, provided that when R30 is NR1R2 or S(=O)$_p$—NR1R2 the NR1R2 is not substituted with O(C=O)O—(NR1"R2")—S(=O)$_p$R3, S(=O)$_p$R3, =N—S(=O)$_p$R3, —N=N—(R1"R2"N)—S(=O)$_p$R3, or =N—N=(R1"R2"N)S(=O)$_p$R3;

each R40 is independently selected from a group consisting of NO$_2$, CN, SO$_3$H, COOH, COOR20, CHO, COR20, OCOR20, =O, R20, OH, OR20, OSiH$_3$, OSi(R20)$_3$, NHCOR20, NR1R2, S(=O)$_p$R3 and a saturated or partly unsaturated monocyclic heterocycle optionally substituted one or more times with R10', provided that when R40 is NR1R2 or S(=O)$_p$R3 the R3 is not substituted with NR1R2 or S(=O)$_p$—NR1R2 and the NR1R2 is not substituted with O(C=O)O—(NR1"R2")—S(=O)$_p$R3, —S(=O)$_p$R3, =NS(=O)$_p$R3, —N=N—(R1"R2"N)—S(=O)$_p$R3, or =N—N=(R1"R2"N)—S(=O)$_p$R3;

each R50 is independently selected from a group consisting of NO$_2$, CN, SO$_3$H, COOH, COOR20, CHO, COR20, OCOR20, =O, R20, OH, OR20, OSiH$_3$, OSi(R20)$_3$, NHCOR20, NR1R2, S(=O)$_p$R3, and a saturated or partly unsaturated monocyclic heterocycle optionally substituted one or more times with R10', provided that when R50 is NR1R2 or S(=O)$_p$R3 the R3 is not substituted with NR1R2 or S(=O)$_p$—NR1R2 and the NR1R2 is not substituted with O(C=O)O—(NR1"R2")—S(=O)$_p$R3, S(=O)$_p$R3, =NS(=O)$_p$R3, —N=N—(R1"R2"N)—S(=O)$_p$R3, or =N—N=(R1"R2"N)—S(=O)$_p$R3; and each p is independently selected from the group consisting of 0, 1 and 2;

provided that at least one of R1, R2 and R3 is linked to the polymer

In particular, disclosed embodiments relate to use of a compound of formula (I) or a polymer comprising one or more repeating units, wherein at least one of the repeating units comprises a sulfenamide moiety of formula (II) as a flame retardant, wherein L1, L2, and L3 are each independently selected from a group consisting of a bond, C$_{1-10}$-alkylenyl, —(C=O)—, O, NH, and NR20;

each R1 and R2 is independently selected from a group consisting of H, S(=O)$_p$R3, C$_{1-30}$-alkyl, C$_{3-7}$-cycloalkyl optionally substituted one or more times with R10, C$_{2-30}$-alkenyl, C$_{2-30}$-alkynyl, C$_{1-10}$-alkylenyl-X—C$_{1-20}$-alkyl, C$_{1-10}$-alkylenyl-X—C$_{1-7}$-cycloalkyl optionally substituted one or more times with R10, a saturated or partly unsaturated mono- or bicyclic heterocycle optionally substituted one or more times with R10, and a mono- or bicyclic aryl or heteroaryl optionally substituted one or more times with R10; or L1, L2, R1, and R2 together with the N atom they are attached to form a NR1R2 group selected from a group consisting of a saturated or partly unsaturated mono- or bicyclic heterocycle optionally substituted one or more times with R10; a mono-, bi-, tri-, tetra- or pentacyclic heteroaryl optionally substituted one or more times with R10; N=CR1'R2'; and N=S=S;

R3 is selected from a group consisting of C$_{1-30}$-alkyl, C$_{3-7}$-cycloalkyl optionally substituted one or more times with R30, C$_{2-30}$-alkenyl, C$_{2-30}$-alkynyl, NR1R2, a saturated or party unsaturated mono- or bicyclic heterocycle optionally substituted one or more times with R30, and a mono-, bi-, or tricyclic aryl or heteroaryl optionally substituted one or more times with R30;

or

L1, L3, R1, and R3 together with the N atom and the S atom they are attached to form a group selected from a mono-, bi-, or tricyclic heteroaryl optionally substituted one or more times with R40, and a saturated or partly unsaturated mono- or bicyclic heterocycle optionally substituted one or more times with R40; and R2 is as defined above;

or

L1, L2, L3, R1, R2, and R3 together with the S atom and the N atom to which they are attached to form a mono-, bi- or tricyclic heteroaryl optionally substituted one or more times with R50;

each R1' and R2' is independently R1 or R2, respectively, as defined above, or R1' and R2' form together with the C atom they are attached to a CR1'R2' group selected from a group consisting of a C$_{3-7}$-cycloalkyl optionally substituted one or more times with R10, a saturated or partly unsaturated mono- or bicyclic heterocycle optionally substituted one or more times with R10, a mono- or bicyclic aryl or heteroaryl optionally substituted one or more times with R10, X is O, S, NH, NR20, P, Si, or Se;

each R10 is independently selected from a group consisting of NO$_2$, CN, SO$_3$H, COOH, COOR20, CHO, COR20, OCOR20, =O, R20, NHCOR20, NH$_2$, NHR20, N(R20)$_2$, OH, OR20, OSiH$_3$, OSi(R20)$_3$, S(=O)$_p$R3, =N—S(=O)$_p$R3, —N=N(R1"R2"N)—S(=O)$_p$R3, and =N—N=(R1"R2"N)—S(=O)$_p$R3, wherein R1"R2"N forms a monocyclic saturated heterocycle optionally substituted with one or more R10'; provided that when R10 is S(=O)$_p$R3, =N—S(=O)$_p$R3, —N=N—(R1"R2"N)—S(=O)$_p$R3, or =N—N=(R1"R2"N)— S(=O)$_p$R3, the R3 is not substituted with NR1R2 or SNR1R2;

each R10' is independently selected from a group consisting of NO$_2$, CN, SO$_3$H, COOH, COOR20, CHO, COR20, OCOR20, =O, R20, NHCOR20, NH$_2$, NHR20, N(R20)$_2$, OH, OR20, OSiH$_3$, and OSi(R20)$_3$;

each R20 is independently selected from a group consisting of C$_{1-30}$-alkyl, C$_{2-30}$-alkenyl, C$_{2-30}$-alkynyl, aryl, C$_{1-10}$-alkylenyl-aryl, heteroaryl, and C$_{1-10}$-alkylenyl-heteroaryl, wherein the aryl or heteroaryl is optionally substituted one or more times with C$_{1-4}$-alkyl, NO$_2$, CN, NH$_2$, NMe$_2$, OH and/or OMe;

each R30 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, and $S(=O)_p$—NR1R2, provided that when R30 is NR1R2 or $S(=O)_p$—NR1R2 the NR1R2 is not substituted with $S(=O)_pR3$, =N—$S(=O)_pR3$, —N=N(R1"R2"N)—$S(=O)_pR3$, or =N—N=(R1"R2"N)—$S(=O)_pR3$;

each R40 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, $S(=O)_pR3$ and a saturated or partly unsaturated monocyclic heterocycle optionally substituted one or more times with R10', provided that when R40 is NR1R2 or $S(=O)_pR3$ the R3 is not substituted with NR1R2 or $S(=O)_p$—NR1R2 and the NR1R2 is not substituted with —$S(=O)_pR3$, =N—$S(=O)_pR3$, —N=N—(R1"R2"N)$S(=O)_pR3$, or =N—N=(R1"R2"N)—$S(=O)_pR3$;

each R50 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, $S(=O)_pR3$, and a saturated or partly unsaturated monocyclic heterocycle optionally substituted one or more times with R10', provided that when R50 is NR1R2 or $S(=O)_pR3$ the R3 is not substituted with NR1R2 or $S(=O)_p$—NR1R2 and the NR1R2 is not substituted with $S(=O)_pR3$, =N—$S(=O)_pR3$, —N=N—(R1"R2"N)$S(=O)_pR3$, or =N—N=(R1"R2"N)—$S(=O)_pR3$; and each p is independently selected from the group consisting of 0, 1 and 2.

A compound of formula (I) may be used in combination with one or more other compound(s) of formula (I), and/or other flame retardant(s) and/or synergist(s). Similarly a polymer comprising one or more repeating units, wherein at least one of the repeating units comprises a sulfenamide moiety of formula (II) may be used in combination with one or more other polymer(s) comprising one or more repeating units, wherein at least one of the repeating units comprises a sulfenamide moiety of formula (II), one or more compound(s) of formula (I), and/or other flame retardant(s) and/or synergist(s). The combined use of compound of formula (I) and/or polymer comprising one or more repeating units, wherein at least one of the repeating units comprises a sulfenamide moiety of formula (II), and other flame retardants improves synergistically the flame retarding efficacy of the other flame retardants. The compounds of formula (I) and polymers comprising one or more repeating units, wherein at least one of the repeating units comprises a sulfenamide moiety of formula (II), may have a synergistic effect on other conventional flame retardants. In such cases their use allows a significant reduction of the amounts needed when applying conventional flame retardants and/or better flame retardant classification can be reached than either one alone or at the same amount. The amount is chosen in a manner known in the art so that an industrially acceptable flame retarding property is provided to the polymeric substrate. Naturally the effective amount varies depending i.e., on the used polymeric substrate and use of application of the obtained flame retarded polymeric substrate and can be determined by a skilled person. As an example the amount is from 0.1 to 20% w/w based on the polymeric substrate, e.g., from 0.1 to 10% w/w. If synergistic mixtures with the other compounds of formula (I) or other flame retardants other than compounds of formula (I) as described herein are used, then naturally lower amounts of a compound of formula (I) and conventional flame retardants are needed to achieve an effective flame retarding effect. The term effective amount thus includes also the lower amounts used in such synergistic mixtures.

The term "$C_{1-30}$-alkyl" as used herein and hereafter as such or as part of another group is an aliphatic linear or branched hydrocarbon group having suitably 1 to 30, e.g., 1 to 7, carbon atoms in the alkyl moiety and thus $C_{1-7}$-alkyl includes methyl, ethyl, n-propyl, isopropyl, n-butyl, sec-butyl, isobutyl, tert-butyl, and branched and straight chain pentyl, hexyl and heptyl.

The term "$C_{1-10}$-alkylenyl" as used herein and hereafter, is a divalent group derived from a straight or branched chain hydrocarbon of having suitably 1 to 10 carbon atoms. Representative examples of an alkylenyl group include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "$C_{2-30}$-alkenyl" as used herein and hereafter is an unsaturated linear or branched hydrocarbon group having at least one olefinic double bond between any two carbon atoms and having suitably 1 to 30, e.g., 1 to 7, carbon atoms in the alkenyl moiety, such as ethenyl, 1-propenyl, 2-propenyl, 3-propenyl, butenyl, pentenyl, and hexenyl.

The term "$C_{2-30}$-alkynyl" as used herein is an unsaturated linear or branched hydrocarbon group having at least one olefinic triple bond between any two carbon atoms and having suitably 1 to 30, e.g., 1 to 7, carbon atoms in the alkenyl moiety, such as ethynyl, propynyl, butynyl, pentynyl, and hexynyl.

The term "$C_{3-7}$-cycloalkyl" as used herein and hereafter refers to cycloalkyl groups having 3 to 7 carbon atoms and thus includes cyclopropyl, cyclobutyl, cyclopentyl, cyclohexyl, and cycloheptyl.

The term "a saturated or partly unsaturated mono- or bicyclic heterocycle" used herein and refers to aliphatic or partly unsaturated ring comprising one or more heteroatoms, e.g., 1 to 4 heteroatoms, as ring atoms, where the heteroatoms include at least the heteroatoms denoted in the same context and optionally one or more further heteroatom(s). Each heteroatom is independently selected from N, S, O, P, Si and Se e.g., from N, O and S, unless denoted otherwise. Examples of saturated monocyclic heterocycles include, but are not limited to, pyrrolidinyl, tetrahydrofuranyl, imidazolidinyl, pyrazolidinyl, piperidinyl, tetrahydropyranyl, tetrahydrothiopyranyl, piperazinyl, morpholinyl, thiomorpholinyl, dioxanyl, and dithianyl.

The term "aryl" used herein and hereafter refers to mono- and polycyclic aromatic hydrocarbons. Examples of aryls include but are not limited to phenyl and naphtalenyl. The aryl can be substituted with one or more substituents as defined herein and hereafter.

The term "heteroaryl" used herein and hereafter refers to an mono- and polycyclic aromatic ring comprising one or more heteroatoms, e.g., 1 to 4 heteroatoms, as ring atoms, where the heteroatoms include at least the heteroatoms denoted in the same context and optionally one or more further heteroatom(s). Each heteroatom is independently selected form N, O, S, P, Si, and Se, e.g., from N, O and S, unless denoted otherwise. The heteroaryl group need only have some degree of aromatic character. The heteroaryl can be substituted with one or more substituents as defined herein and hereafter. Examples of monocyclic heteroaryls include, but are not limited to, pyrrolyl, furyl, thienyl, phospholyl, silolyl, triazolyl, furazanyl, oxadiazolyl, thiadiazolyl, dithiazolyl, tetrazolyl, imidazolyl, pyridinyl, pyranyl, thiopyranyl, salinyl, phosphinine, pyrazinyl, pyrimidinyl, pyridazinyl, oxazine, thiazine, diozine, dithiine, triazinyl, and tetrazinyl. Examples of bicyclic heteroaryls include indolyl, quinolinyl, benzoazepinyl, benzothiazolyl and other bicyclic aryls resulting from the fusion of a monocyclic heteroaryl and benzene ring or another monocyclic heteroaryl. Examples of tricyclic heteroaryls include carbazolyl, acridinyl, other tricyclic aryls resulting from the fusion of a bicyclic heteroaryl as defined above and a benzene ring or another monocyclic heteroaryl.

When any variable occurs more than one time in any constituent or in formula (I) its definition on each occurrence is independent of its definition at every other occurrence. Further, combinations of substituents and/or variables are permissible only if such combination results a stable compound.

As used herein, a monomer that is part of the main chain (or backbone) of a polymer is a repeating unit that is connected on at least two ends to the polymer chain. It will be appreciated that the moiety can be the only moiety in the backbone monomer. Alternatively, the moiety can be one of a plurality of moieties in the backbone of the monomer: The term "pendant" as used herein, refers to a moiety that is attached at only one end to a polymer backbone. It is to be understood that the moiety may be directly connected to the polymer backbone or there may be additional moieties e.g., linker groups, L' in between the moiety and the polymer backbone. The attachment can come at any of the R1, R2 and R3 groups. The linker group L' may be selected from the group consisting of a bond, —O—, —NH—, —(C=O)—, —O—(C=O)—, —(C=O) O—, —N(C=O), —(C=O)—N—, —O—(C=O)—NH—, —NH—(C=O)—O—, —O—(C=O)—$C_{1-10}$-alkylenyl-O. —O—$C_{1-10}$-alkylenyl-(C=O)—O—, —O(C=O)—O)—, —Si—, a mono- or bicyclic aryl or heteroaryl optionally substituted one or more times with R10, wherein R10 is as defined herein.

The term "optionally substituted" as used herein and hereafter denotes that the group it refers to is either unsubstituted or substituted independently with one or more, e.g., 1, 2, 3 or 4, substituent(s) attached at any available atom to produce a stable compound, In general "substituted" refers to a substituent group as defined herein in which one or more bonds to a hydrogen atom contained therein are replaced by a bond to a non-hydrogen atom unless otherwise denoted.

"Optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The compounds of formula (I) and the polymers comprising one or more repeating units, wherein at least one of the repeating units comprises a sulfenamide moiety of formula (II) and bears a specific S—N core which has not been disclosed in the prior art as possessing any flame retarding activity. The compounds of formula (I), except some specific 2-benzothiazole sulfenamide derivatives, and the polymers comprising one or more repeating units, wherein at least one of the repeating units comprises a sulfenamide moiety of formula (II) have not been disclosed in prior art as possessing any synergistic flame retarding activity.

Preferred compounds of formula (I) or polymers comprising one or more repeating units, wherein at least one of the repeating units comprises a sulfenamide moiety of formula (II), are those where each p is 0.

Particularly preferred compounds of formula (I) or polymers comprising one or more repeating units, wherein at least one of the repeating units comprises a sulfenamide moiety of formula (II), are those where L1, L2, and L3 are each a bond.

Further compounds of formula (I) or polymers comprising one or more repeating units, wherein at least one of the repeating units comprises a sulfenamide moiety of formula (II), are those where each p is 0 and L1, L2, and L3 are each a bond.

In an example, a compound of formula (I) or a polymer comprising one or more repeating units, wherein at least one of the repeating units comprises a sulfenamide moiety of formula (II), wherein L1, L2, and L3 are each a bond;

each R1 and R2 is independently selected from a group consisting of SR3, $C_{1-30}$-alkyl, $C_{3-7}$-cycloalkyl optionally substituted one or more times with R10, a saturated monocyclic heterocycle comprising 1 to 4 heteroatom(s) each independently selected from N, S, and O and optionally substituted one or more times with R10, and a mono- or bicyclic aryl or heteroaryl comprising 1 to 4 heteroatom(s) each independently selected from N, S, and O and optionally substituted one or more times with R10; or L1, L2, R1, and R2 together with the N atom they are attached to form a NR1R2 group selected from a saturated monocyclic heterocycle, optionally further comprising 1 to 4 heteroatom(s) each independently selected from N, S, and O and optionally substituted one or more times with R10; a mono-, bi-, or tricyclic heteroaryl optionally further comprising 1 to 4 heteroatom(s) each independently selected from N, S and O and optionally substituted one or more times with R10; N=CR1'R2'; and N=S=S;

R3 is selected from a group consisting of $C_{1-30}$-alkyl; $C_{3-7}$-cycloalkyl, optionally substituted one or more times with R30; NR1R2; a saturated monocyclic heterocycle comprising 1 to 4 heteroatom(s) each independently selected from N, S, and O and optionally substituted one or more times with R30; and a mono-, bi-, or tricyclic aryl or heteroaryl comprising 1 to 4 heteroatoms each independently selected from N, S and O, optionally substituted one or more times with R30;

or

L1, L3, R1, and R2 together with the N atom and the S atom they are attached to form a group selected from a mono-, bi-, or tricyclic heteroaryl optionally further comprising 1 to 3 heteroatoms selected from N, S and O and optionally substituted one or more times with R40, and a saturated mono- or bicyclic hetero ring system optionally further comprising 1 to 3 heteroatoms selected from N, S and O and optionally substituted one or more times with R40; and R2 is as defined above;

or

L1, L2, L3, R1, R2, and R3 together with the S atom and the N atom to which they are attached to form a bi- or tricyclic heteroaryl optionally further comprising 1 to 4 heteroatoms each independently selected from N, S and O and optionally substituted one or more times with R50;

each R1' and R2' is independently R1 or R2, respectively, as defined above, or R1' and R2' form together with the C atom they are attached to a CR1'R2' group selected from a group consisting of a $C_{3-7}$-cycloalkyl optionally substituted one or more times with R10, a saturated or partly unsaturated mono- or bicyclic heterocycle optionally substituted one or more times with R10, a mono- or bicyclic aryl or heteroaryl optionally substituted one or more times with R10, each R10 is independently selected from a group consisting of $NO_2$, CN, $SO_3H$, COOH, COOR20, CHO, COR20, OCOR20, =O, R20, NHCOR20, NH₂, NHR20, N(R20)₂, OH, OR20, SR3, —N=N—(R1"R2"N)—SR3, and =N—N=(R1"R2"N)—SR3, wherein R1"R2"N forms a monocyclic saturated heterocycle optionally substituted with one or more R10'; provided that when R10 is SR3, —N=N—(R1"R2"N)—SR3, or =N—N=(R1"R2"N)—SR3, the R3 is not substituted with NR1R2 or SNR1R2;

each R10' is independently selected from a group consisting of NO₂, CN, SO₃H, COOH, COOR20, CHO, COR20, OCOR20, =O, R20, NHCOR20, NH₂, NHR20, N(R20)₂, OH, and OR20;

each R20 is independently selected from a group consisting of $C_{1-30}$-alkyl, $C_{2-30}$-alkenyl, $C_{2-30}$-alkynyl, aryl, $C_{1-10}$-alkylenyl-aryl, heteroaryl, and $C_{1-10}$-alkylenyl-heteroaryl, wherein the aryl or heteroaryl is optionally substituted one or more times with $C_{1-4}$-alkyl, NO₂, CN, NH₂, NMe₂, OH and/or OMe;

each R30 is independently selected from a group consisting of NO₂, CN, SO₃H, COOH, COOR20, CHO, COR20, OCOR20, =O, R20, OH, OR20, NHCOR20, NR1R2, and SNR1R2, provided that when R30 is NR1R2 or SNR1R2 the R1 and R2 are not substituted with SR3, —N=N—(R1"R2"N)—SR3, or =N—N=(R1"R2"N)—SR3;

each R40 is independently selected from a group consisting of NO₂, CN, SO₃H, COOH, COOR20, CHO, COR20, OCOR20, =O, R20, OH, OR20, NHCOR20, NR1R2, SR3 and a saturated or partly unsaturated monocyclic heterocycle optionally substituted one or more times with R10', provided that when R40 is NR1R2 or SR3 the R3 is not substituted with NR1R2 or SNR1R2 and the R1 and R2 are not substituted with SR3, —N=N—(R1"R2"N)—SR3, or =N—N=(R1"R2"N)—SR3;

each R50 is independently selected from a group consisting of NO₂, CN, SO₃H, COOH, COOR20, CHO, COR20, OCOR20, =O, R20, OH, OR20, NHCOR20, NR1R2, SR3, and a saturated or partly unsaturated monocyclic heterocycle optionally substituted one or more times with R10', provided that when R50 is NR1R2 or SR3 the R3 is not substituted with NR1R2 or SNR1R2 and the R1 and R2 are not substituted with SR3, —N=N—(R1"R2"N)—SR3, or =N—N=(R1"R2"N)—SR3.

Compounds of formula (I) or polymers comprising one or more repeating units, wherein at least one of the repeating units comprises a sulfenamide moiety of formula (II), wherein NR1R2 forms a ring are particularly good flame retardants. In particular a heteroaryl group increases the thermal stability of the compounds of formula (I). In one example, disclosed embodiments relate to a compound of formula (I), wherein R1 and R2 together with the N atom they are attached to form a monocyclic, bicyclic or tricyclic heteroaryl, optionally substituted one or more times with R20. Advantageously the aromatic ring system is carbazolyl, optionally substituted one or more times with R20. In this example, R3 is as defined above, e.g., a mono or bicyclic aromatic ring system, optionally substituted one or more times with R30 as defined above, e.g., R3 is phenyl optionally substituted one, two or three times with R20, e.g., R3 is selected from a group consisting of phenyl, methoxyphenyl, nitrophenyl, methylphenyl, and trimethylphenyl.

A particular example of a compound of formula (I) of the disclosed embodiments, wherein NR1R2 forms an unsaturated or aromatic ring system is a compound of formula (Ia)

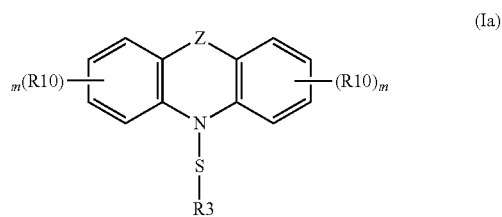

wherein each m is independently 0, 1, 2, 3, or 4, in particular 0, each R10 and R3 is as defined above, and Z is a bond, O, S, NH, NR20, NSR3, CH₂, CHR20, C(R20)₂, or C=O, e.g., a bond, CH₂, CHR20, C(R20)₂, or C=O, e.g., Z is a bond or NSR3.

Z may be a bond and the compound of formula (Ia) is thus a compound of formula (Iaa)

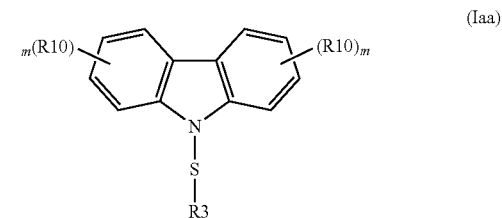

wherein each m is independently 0, 1, 2, 3, or 4, in particular 0, and each R10 and R3 is independently as defined above. R3 may be phenyl or carbazolyl, wherein the phenyl or carbazolyl is optionally substituted one, two, or three times with R30 as defined above; each R30 is advantageously independently selected from the group consisting of R20, NHCOR20, OH, OR20, N(R20)₂, and NR1R2; wherein R20 is as defined above, e.g., methyl; and each R1 and R2 are as defined above; each R30 may be independently methyl or methoxy.

Alternatively Z is N—SR3 and the compound of formula (Ia) is thus a compound of formula (Iab)

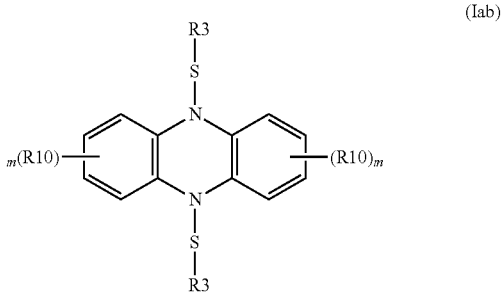

wherein each m is independently 0, 1, 2, 3, or 4, in particular 0, and each R10 and R3 is independently as defined above. R3 may be aryl, e.g., R3 is selected form a group consisting of methoxyphenyl, nitrophenyl, methylphenyl and trimethylphenyl.

In still further suitable example wherein NR1R2 forms an unsaturated or aromatic ring system is a compound of formula (Iac)

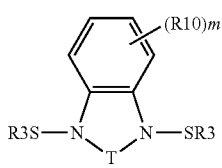

(Iac)

wherein m is 0, 1, 2 3, or 4, in particular 0, and T is selected from the group consisting of C=O, C=S, C=N—SR3, N—SR3, N, S, O and P; and each R3 and R10 is independently as defined above. R3 may be aryl, e.g., R3 is selected form a group consisting of methoxyphenyl, nitrophenyl, methylphenyl and trimethylphenyl. T may be C=O.

In another advantageous example, at least one of R1 and R2 may be independently selected from mono- or bicyclic aromatic or unsaturated carbon or hetero ring systems optionally substituted one or more times with R10. At least one of R1 and R2 may be selected from a group consisting of phenyl, naphtalenyl. Aryl and heteroaryl groups increase the thermal stability of the flame retardant compounds of formula (I) or polymers comprising one or more repeating units, wherein at least one of the repeating units comprises a sulfenamide moiety of formula (II).

In a further example, the compound of formula (I) is a compound of formula (Ib)

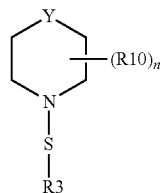

(Ib)

wherein n is from 0 to 8, e.g., 0 to 4; Y is selected from a group consisting of a bond, CH$_2$, CHR10, C(R10)$_2$, N—SR3, C=O, C=N—SR3, and C=N—N(R1"R2"N)SR3, wherein R1"R2"N forms a monocyclic saturated heterocycle as defined above; and each R10 and R3 is as defined above. In this example, n may be 4 and each R10 may be methyl or n may be 2 and each R10 may be =O. In this example, each R3 may be independently C$_{1-7}$-alkyl or a mono- or bicyclic aryl, optionally substituted one or more times with R30 as defined above, e.g., phenyl, methylphenyl, trimethylphenyl, nitrophenyl, methoxyphenyl, pyridinyl, or butyl.

In one suitable example, the compound of formula (I) is a compound of formula (Iba)

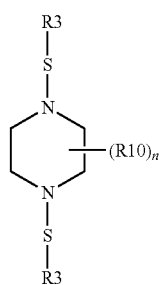

(Iba)

wherein n is 0 to 8, e.g., 2; R3 is as defined above, phenyl optionally may be substituted one or more times with R30; and each R10 is as defined above, e.g., alkyl, in particular, methyl.

In an example of the above the compound of formula (I) is a compound of formula (Ibb)

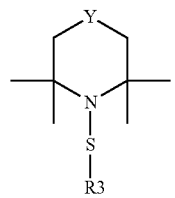

(Ibb)

wherein Y is C=O, N—SR3, O, or S, and each R3 is independently as defined above.

In a particular example of the above the compound of formula (I) is a compound of formula (Ibc)

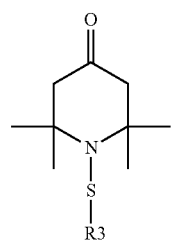

(Ibc)

wherein R3 is as defined above. In this example, R3 may be a mono or bicyclic aryl, optionally substituted one or more times with R30 as defined above. R3 may be phenyl or pyridinyl, which phenyl or pyridinyl may be optionally substituted one, two or three times with R30 as defined above. Each R30 may be selected from a group consisting of methyl, methoxy, and NO$_2$.

In a further example of the above, the compound of formula (I) is a compound of formula (Ibd)

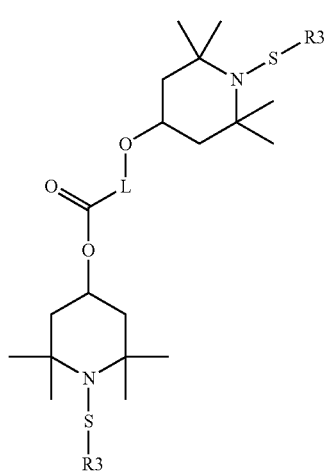

(Ibd)

wherein each R3 is as defined above and L is bond or C$_{1-10}$-alkylenyl-(C=O)—. In this example, R3 may be a mono or bicyclic aryl, optionally substituted one or more times with R30 as defined above. R3 may be phenyl or pyridinyl, which phenyl or pyridinyl is optionally substituted one, two or three times with R30 as defined above. Each R30 may be selected from a group consisting of methyl, methoxy, and NO$_2$. R3 may be phenyl.

Compounds of formula (I) and the polymers comprising one or more repeating units, wherein at least one of the repeating units comprises a sulfenamide moiety of formula (II), wherein R1, R2 and/or R3 is an aryl and/or heteroaryl are another example particularly good flame retardants. The aromatic group increases the thermal stability of the compounds and polymers.

In an advantageous example, a compound of formula (I) or a polymer comprising one or more repeating units is provided, wherein at least one of the repeating units comprises a sulfenamide moiety of formula (II), wherein R3 is a mono- bi- or tricyclic aryl or heteroaryl, optionally substituted one or more times with R30. In this example, R3 may be selected from a group consisting of phenyl, naphthyl, pyridyl, indolyl and carbazolyl, each optionally substituted one, two or three times with R30 as defined above.

In still another example, the compound of formula (I) may be a compound of formula (Ic)

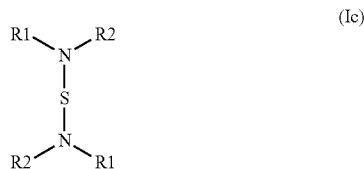

wherein R1 and R2 are each independently as defined above. In this example, each R1 and R2 is independently selected from branched C$_{3-30}$-alkyl, C$_{3-7}$-cycloalkyl, saturated mono- or bicyclic heterocycle optionally substituted one or more times with R10, a mono- or bicyclic aryl or heteroaryl optionally substituted one or more times with R10; or R1 and R2 together with the N atom they are attached to form a saturated mono- or bicyclic heterocycle optionally further comprising 1 to 4 heteroatoms selected from N, S and O and optionally substituted one or more times with R10; or a mono-, bi-, tricyclic heteroaryl optionally further comprising 1 to 4 heteroatoms selected from N, S and O and optionally substituted one or more times with R10, and wherein each R10 is independently as defined above. R1 and R2 together with the N atom they are attached to may form a group selected from morpholinyl, phtalimidyl, and carbazolyl.

In another example, L1 and L2 may both be a bond and R1 and R2 may form together with the N atom they are attached to a saturated monocyclic heterocycle optionally further comprising 1 heteroatom selected from N or O and consisting of 5 or 6 ring atoms and optionally substituted one or more times with R10 as defined above, e.g., each R10 is independently selected from methyl and =O; or monocyclic, bicyclic or tricyclic heteroaryl consisting of 6 to 14 ring atoms, and optionally substituted one or more times with R10, for example, R10 may be =O.

In a particular example of the above the compound of formula (I) is a compound of formula (Id)

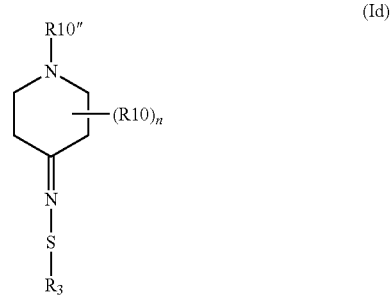

wherein n is 0 to 8, R10" is H or R10, and each R10 and R3 are independently as defined above. In this example, R3 may be a mono or bicyclic aryl, optionally substituted one or more times with R30 as defined above. R3 may be phenyl or pyridinyl, which phenyl or pyridinyl may be optionally substituted one, two or three times with R30 as defined above. Further, optionally, each R30 is selected from a group consisting of methyl, methoxy, and NO$_2$. In this example, R10" may be H, methyl, branched C$_{3-7}$-alkyl, C$_{1-6}$-alkoxy, phenyl, OSiH$_3$, or OSi(Me)$_3$.

In an another further suitable example, the compound of formula (I) is a compound of formula (Ie)

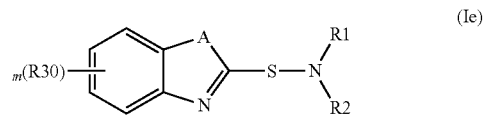

wherein m is 0 to 4, A is S, O or NH, and R1, R2, and R30 are each independently as defined above. R1 and R2 may each independently branched C$_{3-7}$-alkyl or C$_{3-7}$-cycloalkyl, or one of R1 and R2 is SR3, wherein R3 is as defined above, e.g., a mono- or bicyclic aryl or heteroaryl, and the other of R1 and R2 is branched C$_{3-7}$-alkyl or C$_{3-7}$-cycloalkyl.

In a further suitable example, the compound of formula (Ie) is a compound of formula (Iea)

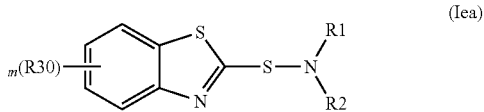

wherein m is 0 to 4, and R1, R2, and R30 are each independently as defined above. R1 and R2 may be each independently branched C$_{3-7}$-alkyl or C$_{3-7}$-cycloalkyl, or one of R1 and R2 is SR3, wherein R3 is as defined above, e.g., a bicyclic aryl or heteroaryl, and the other of R1 and R2 is branched C$_{3-7}$-alkyl or C$_{3-7}$-cycloalkyl.

In a still another further suitable example, the compound of formula (I) is a compound of formula (If)

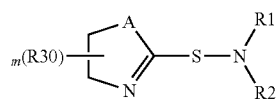 (If)

wherein m is 0 to 4, A is S, O or NH, and R1, R2, and R30 are each independently as defined above. R1 and R2 may be each independently branched $C_{3-7}$-alkyl or $C_{3-7}$-cycloalkyl, or one of R1 and R2 is SR3, wherein R3 is as defined above, e.g., a mono- or bicyclic aryl or heteroaryl, and the other of R1 and R2 is branched $C_{3-7}$-alkyl or $C_{3-7}$-cycloalkyl.

In a further suitable example, the compound of formula (If) is a compound of formula (Ifa)

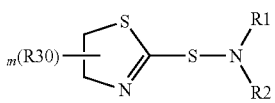 (Ifa)

wherein m is 0 to 4, and R1, R2, and R30 are each independently as defined above. R1 and R2 may be each independently branched $C_{3-7}$-alkyl or $C_{3-7}$-cycloalkyl, or one of R1 and R2 is SR3, wherein R3 is as defined above, e.g., a bicyclic aryl or heteroaryl, and the other of R1 and R2 is branched $C_{3-7}$-alkyl or $C_{3-7}$-cycloalkyl.

In still another suitable example, the compound of formula (I) is a compound of formula (Ig)

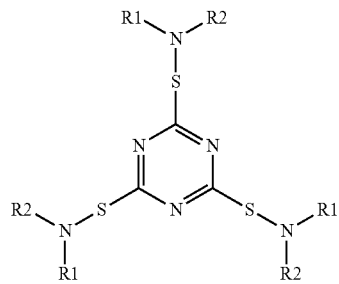 (Ig)

wherein each R1 and R2 is independently as defined above, each R1 and R2 together with the nitrogen they are attached to may form a monocyclic aliphatic ring optionally further comprising one heteroatom selected from N and O, and consisting of 5 to 6 ring atoms, e.g., the ring is morpholinyl.

In still another further suitable example, the compound of formula (I) is a compound of formula (Ih)

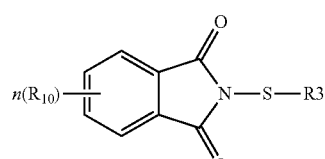 (Ih)

wherein each R10 and R3 are independently as defined above and n is 0 to 4, e.g., 0 or 1. In this example, each R3 may be independently $C_{1-7}$-alkyl or a mono- or bicyclic aryl, optionally substituted one or more times with R30 as defined above, e.g. phenyl, methylphenyl, trimethylphenyl, nitrophenyl, methoxyphenyl, pyridinyl, or butyl.

In a suitable example, the compound of formula (I) is a compound of formula (Ii)

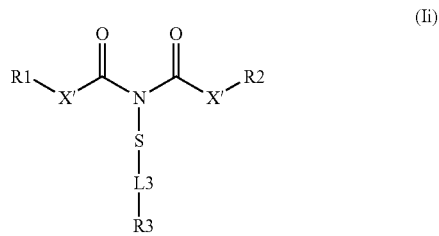 (Ii)

wherein R1, R2, R3 and L3 are independently as defined above and X' is N, O or a bond. Optionally, L3 is bond. R1 and R2 may be each independently selected from $C_{1-30}$-alkyl, and an aliphatic or aromatic ring optionally substituted one or more times with R10.

In an advantageous example, a polymer may be provided which comprises one or more repeating units, wherein at least one of the repeating units comprises a sulfenamide moiety of formula (II) is a polymer of formula (IIIa) or (IIIb)

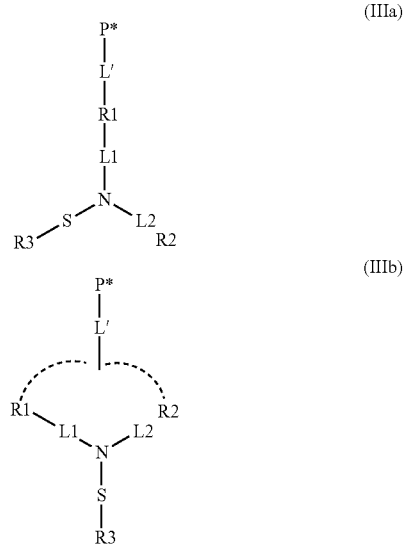

wherein R1, R2, R3, L1, L2 and L' are as defined herein and P* refers to a repeating unit of a polymeric backbone. Optionally, in this example, P* is a repeating unit of a polymeric backbone of a polymer as defined in categories 1 to 21 on pages 27 to 31. In particular in this example in the polymer of formula (IIIb) L1, L2, R1, and R2 together with the N atom they are attached to form a NR1R2 group selected from a group consisting of a saturated or partly unsaturated mono- or bicyclic heterocycle optionally substituted one or more times with R10; and a mono-, or bicyclic heteroaryl optionally substituted one or more times with R10.

In a particular example, a polymer comprising one or more repeating units, wherein at least one of the repeating units comprises a sulfenamide moiety of formula (II) is a polymer of formula (IIIc)

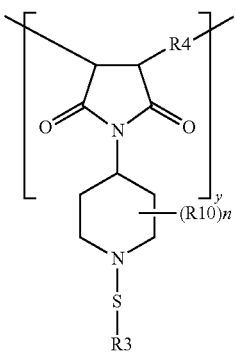

(IIIc)

wherein R3 and R10 are as defined herein, n is 0 to 8, e.g., 0 to 4, R4 is $C_{1-30}$-alkylenyl and y refers to number of repeating units of the polymer, e.g., y is from 3 to 3000. In this example, R3 may be a mono- or bicyclic aryl or heteroaryl, e.g., phenyl, optionally substituted one or more times with R30 as defined herein. Fore example, R4 may be —$CH_2CH[(CH_2)_{17-21}CH_3]$—.

In any one of the above examples NR1R2 may be suitably selected from the group consisting of:

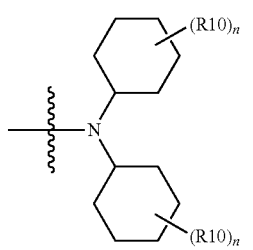 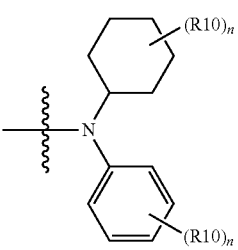

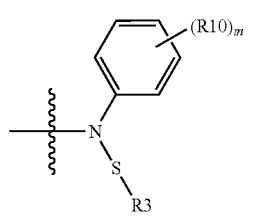 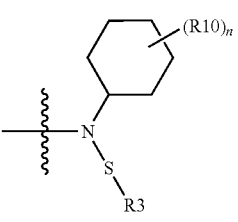

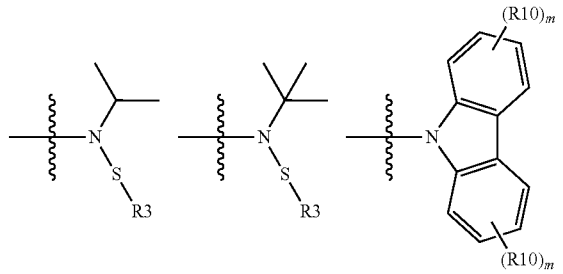

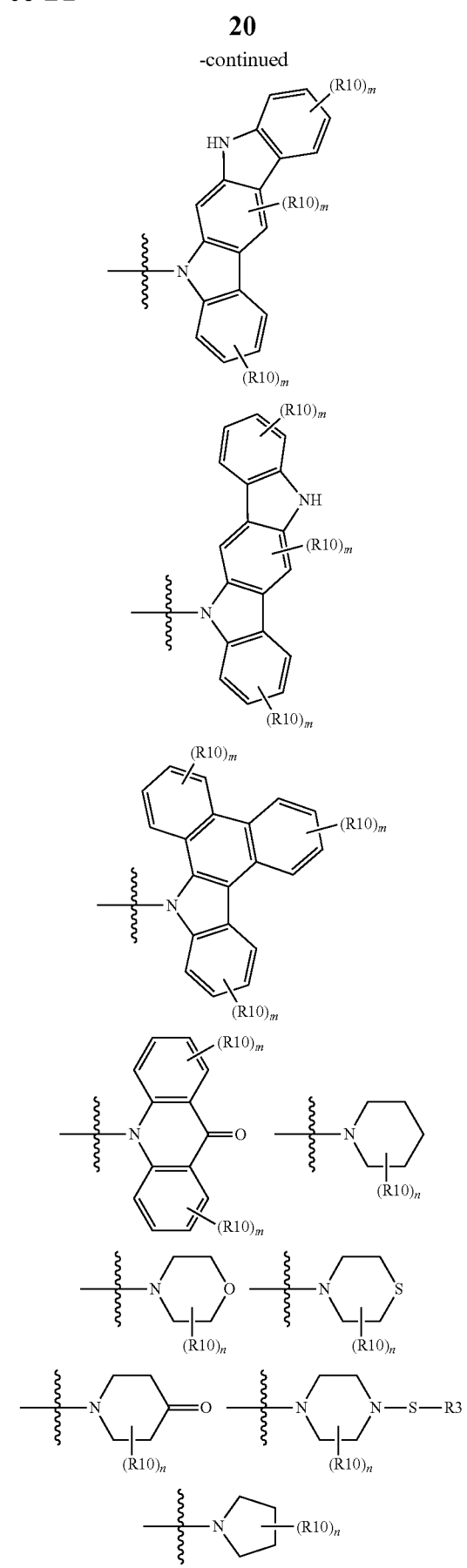

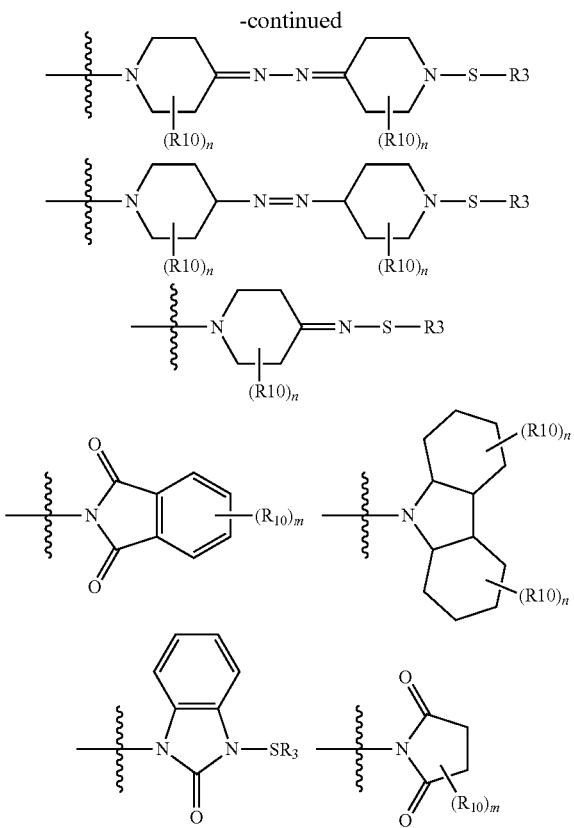

In an example, the compound of formula (I) may be selected from a group consisting of:
2,2,6,6-tetramethyl-1-(phenylthio)piperidin-4-one (1);
1-((4-methoxyphenyl)thio)-2,2,6,6-tetramethylpiperidin-4-one (2);
2,2,6,6-tetramethyl-1-((4-nitrophenyl)thio)piperidin-4-one (3);
1-(2-nitrophenylthio)-2,2,6,6-tetramethylpiperidin-4-one (4);
2,2,6,6-tetramethyl-1-(4-methylphenylthio)piperidin-4-one (5);
1-(2,4,6-trimethylphenylthio)-2,2,6,6-tetramethylpiperidin-4-one (6);
1-(2-pyridylthio)-2,2,6,6-tetramethylpiperidin-4-one (7);
1,2-bis(2,2,6,6-tetramethyl-1-(phenylthio)piperidin-4-ylidene)hydrazine (8);
2,2,6,6-tetramethyl-1-(phenylthio)-4-piperidyl methacrylate (9);
1-[(1-disulfenylideneamino)sulfenyl-2'2'6'6-tetramethylpiperidin-4-one (10);
trans-2,5-dimethyl-1,4-bis(phenylthio)piperazine (11);
1-butylsulfanyl-2'2'6'6-tetramethylpiperidine (12);
4'-thiobis-morpholine (13);
1,1'-thiobis-(2,6-dimethyl)piperidine (14);
1,1'-thiobis-(2,2,6,6-tetramethyl)piperidine (15);
N-1,5,9-((4-methoxyphenyl)thio))-bis-(2,2,6,6-tetramethyl-4-piperidyl)amine (16);
1,1'-thiobis phtalimide (17);
1,1'-thiobis-carbazole (18);
2-[(4-methoxyphenyl)thio]-1H-Isoindole-1,3(2H)-dione (19);
9-(phenylthio)-9H-carbazole (20),
9-[(4-methoxyphenyl)thio]-9H-carbazole (21);
N-2-naphthalenyl-N-phenyl-4-methylbenzenesulfenamide (22);
N-bis[4-(1-methyl-1-phenylethyl)phenyl]-4-methylbenzenesulfenamide (23);
N-cyclohexyl-S-phenyl-N-(phenylthio)thiohydroxylamine (24);
2,4,6-tris(4-morpholinylthio)-[1,3,5]-triazine (25);
S-(benzo[d]thiazol-2-yl)-N,N-diisopropylthiohydroxylamine (26);
S-(benzo[d]thiazol-2-yl)-N,N-dicyclohexylthiohydroxylamine (27);
S-(benzo[d]thiazol-2-yl)-N-(benzo[d]thiazol-2-ylthio)-N-(tert-butyl)thiohydroxylamine (28);
benzo[c][1,2,5]thiadiazole (29);
3-(piperazin-1-yl)benzo[d]isothiazole (30);
5-nitrobenzo[c]isothiazol-3-amine (31);
3-phenyl-1,2,4-thiadiazol-5-amine (32);
bis(2,2,6,6-tetramethyl-1-(phenylthio)piperidin-4-yl)decanedioate (33);
bis(2,2,6,6-tetramethyl-1-(phenylthio)piperidin-4-yl) carbonate (34); and
1,3-bis(phenylthio)-1H-benzo[d]imidazol-2(3H)-one (35).

In an example, the polymer comprising one or more repeating units, wherein at least one of the repeating units comprises a sulfenamide moiety of formula (II), may be poly[3-methyl-4-(2-methyldocosyl)-1-(2,2,6,6-tetramethyl-1-(phenylthio)piperidin-4-yl)pyrrolidine-2,5-dione](36).

Compounds of formula (I) and/or a polymer comprising one or more repeating units, wherein at least one of the repeating units comprises a sulfenamide moiety of formula (II) can be added to any material which flame properties need to be modified. Typically this material is a polymeric material, meaning either a polymer or a plastic material comprising a polymer and additives. The compound of formula (I) can be used either alone or together with one or more compound(s) of formula (I). The polymer comprising one or more repeating units, wherein at least one of the repeating units comprises a sulfenamide moiety of formula (II) can be used either alone or together with one or more other polymer(s) comprising one or more repeating units, wherein at least one of the repeating units comprises a sulfenamide moiety of formula (II). The compound(s) of formula (I) and/or polymer(s) comprising one or more repeating units, wherein at least one of the repeating units comprises a sulfenamide moiety of formula (II) can further be used in combination with one or more other known flame retardant compound(s). Optionally, the other known flame retardant compounds are non-halogenated flame retardants. The compound of formula (I) may be added to a first polymeric substance which may then be used as an additive to another polymeric substance or it may be added to for example a coating material in order to enhance the flame properties of the final product. The present flame retardant compound may also be added directly to the polymeric substance used for the manufacture of the final product. The addition can be effected at any stage, for example during the polymerisation process of the polymer or during compounding or blending.

Conventional additives other than flame retardants can also be added to the polymeric substance. Examples include UV absorbers, light stabilisers, antioxidants, colorants etc.

The compounds of formula (I) and the polymers comprising one or more repeating units, wherein at least one of the repeating units comprises a sulfenamide moiety of formula (II) may be outstandingly suitable for imparting flameretarding properties to polymeric substrates i.e., polymers or polymer containing materials, e.g., synthetic polymers, especially thermoplastics. Therefore, a further embodiment relates to a composition, which comprises (a) a compound of the formula (I) as defined herein and (b) a polymer substrate.

A suitable polymer substrate (b) consists of natural and/or synthetic polymers, such as:

1. Polymers of mono- and diolefins, for example polypropylene, polyisobutylene, polybutene-1, poly-4-methylpentene-1, polyvinylcyclohexane, polyisoprene or polybutadiene and also polymerisates of cycloolefins, for example of cyclopentene or norbornene; and also polyethylene (which may optionally be crosslinked), for example high density poly-ethylene (HDPE), high density polyethylene of high molecular weight (HDPE-HMW), high density polyethylene of ultra-high molecular weight (HDPE-UHMW), medium density polyethylene (MDPE), low density polyethylene (LDPE), and linear low density polyethylene (LLDPE), (VLDPE) and (ULDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and di-olefins with one another or with other vinyl monomers, for example ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers, for example ethylene/norbornene (COC), ethylene/1-olefin copolymers wherein the 1-olefin is prepared in situ, propylene/butadiene copolymers, isobutylene/isoprene copolymers, ethylene/vinyl cyclohexene copolymers, ethylene/alkyl acrylate copolymers, ethylene/alkyl methacrylate copolymers, ethylene/vinyl acetate copolymers, ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another or with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide copolymers and mixtures thereof with other polymers, for example polyamides.

4. Polystyrene, poly(p-methylstyrene), poly(α-methylstyrene).

5. Aromatic homopolymers and copolymers derived from vinyl-aromatic monomers, for example styrene, α-methylstyrene, all isomers of vinyltoluene, for example p-vinyltoluene, all isomers of ethylstyrene, propylstyrene, vinylbiphenyl, vinylnaphthalene, vinylan-thracene and mixtures thereof; homopolymers and copolymers can have a syndiotactic, isotactic, hemi-isotactic or atactic stereo structure; preference may given to atactic polymers. Also included are stereo block polymers.

6. Homopolymers and copolymers can have a syndiotactic, isotactic, hemi-isotactic or atactic stereo structure; preference may be given to atactic polymers. Also included are stereo block polymers.

a) Copolymers including the already mentioned vinyl-aromatic monomers and co-monomers selected from ethylene, propylene, dienes, nitriles, acids, maleic anhydrides, maleic acid amides, vinyl acetate, vinyl chloride and acrylic acid derivatives and mixtures thereof, for example styrene/butadiene, styrene/acrylonitrile, styrene/ethylene (interpolymers), styrene/alkyl methacrylate, styrene/butadiene/alkyl acrylate and methacrylate, styrene/maleic anhydride, styrene/acrylonitrile/methyl acrylate; high-impact-strength mixtures consisting of styrene copolymers and another polymer, for example a polyacrylate, a diene polymer or an ethylene/propylene/dieneterpolymer; and also block copolymers of styrene, for example styrene/butadiene/styrene, styrene/isoprene/styrene, styrene/ethylene-butylene/styrene or styrene/ethylene-propylene/styrene.

b) Hydrogenated aromatic polymers prepared by hydrogenation of the polymers mentioned under item 6), especially polycyclohexylethylene (PCHE), often also referred to as polyvinylcyclohexane (PVCH), which is prepared by hydrogenation of atactic polystyrene.

c) Hydrogenated aromatic polymers prepared by hydrogenation of the polymers mentioned under item 6a).

7. Graft copolymers of vinyl-aromatic monomers, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and me-thyl methacrylate on polybutadiene; styrene and maleic anhydride on polybutadiene; styrene, acrylonitrile and maleic anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene ter-polymers, styrene and acrylonitrile on polyalkyl acrylates or polyalkyl methacrylates, styrene and acrylonitrile on acrylate/butadiene copolymers, and mixtures thereof with the copolymers mentioned above under Paragraph 6, such as those known, for example, as so-called ABS, MBS, ASA or AES polymers.

8. Halogen-containing polymers, for example polychloroprene, chlorinated rubber, chlorinated and brominated copolymer of isobutylene/isoprene (halobutyl rubber), chlorinated or chlorosulphonated polyethylene, copolymers of ethylene and chlorinated ethylene, epichlorohydrin homo- and co-polymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.

9. Polymers derived from α,β-unsaturated acids and derivatives thereof, such as polyacrylates and polymethacrylates, or polymethyl methacrylates, polyacrylamides and polyacrylonitriles impact-resistant-modified with butyl acrylate.

10. Copolymers of the monomers mentioned under Paragraph 9 with one another or with other unsaturated monomers, for example acrylonitrile/butadiene co-polymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

11. Polymers derived from unsaturated alcohols and amines or their acyl derivatives or acetals, such as polyvinyl alcohol, polyvinyl acetate, stearate, benzoate or maleate, polyvinylbutyral, polyallyl phthalate, polyallylmelamine; and the copolymers thereof with olefins mentioned under item 1.

12. Homo- and co-polymers of cyclic ethers, such as polyalkylene glycols, polyethylene oxide, polypropylene oxide or copolymers thereof with bisglycidyl ethers.

13. Polyacetals, such as polyoxymethylene, and also those polyoxymethylenes which contain comonomers, for example ethylene oxide; polyacetals modified with thermoplastic polyurethanes, acrylates or MBS.

14. Polyphenylene oxides and sulphides and mixtures thereof with styrene polymers or polyamides.

15. Polyamides and copolyamides derived from diamines and dicarboxylic acids and/or from aminocarboxylic acids or the corresponding lactams, such as polyamide 4, poly-amide 6, polyamide 6/6, 6/10, 6/9, 6/12, 4/6, 12/12, polyamide 1 1, polyamide 12, aromatic polyamides derived from m-xylene, diamine and adipic acid; polyamide 6/I (poly-hexamethylene isophthalimide, MXD (m-xylylenediamine); polyamides prepared from hexamethylenediamine and iso- and/or terephthalic acid and optionally an elastomer as modifier, for example poly-2,4,4-trimethylhexamethylene terephthalamide or poly-m-phenylene isophthalamide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified with EPDM or ABS; and polyamides condensed during processing ("RIM polyamide systems").

Examples of polyamides and copolyamides that can be used are derived from, inter alia, ε-caprolactam, adipic acid, sebacic acid, dodecanoic acid, isophthalic acid, tereph-thalic acid, hexamethylenediamine, tetramethylenediamine, 2-methylpentamethylenediamine, 2,2,4-trimethylhexamethylenediamine, 2,4,4-trimethylhexamethylenediamine, m-xylylenediamine or bis(3-methyl-4-aminocyclohexyl)methane; and also semi-aromatic polyamides such as polyamide 66/61, for example consisting of 70-95% polyamide 6/6 and 5-30% polyamide 6/I; and also tricopolymers in which some of the poly-amide 6/6 has been replaced, for example consisting of 60-89% polyamide 6/6, 5-30% polyamide 6/I and 1-10% of another aliphatic polyamide; the latter may consist of, for example, polyamide 6, polyamide 11, polyamide 12 or polyamide 6/12 units. Such tricopolymers may accordingly be designated polyamide 66/61/6, polyamide 66/61/1 1, polyamide 66/61/12, polyamide 66/61/610 or polyamide 66/61/612.

16. Polyureas, polyimides, polyamide imides, polyether imides, polyester imides, poly-hydantoins and polybenzimidazoles.

17. Polyesters derived from dicarboxylic acids and dialcohols and/or from hydroxycarbox-ylic acids or the corresponding lactones, such as polyethylene terephthalate, polypropylene terephthalate, polybutylene terephthalate, poly-1,4-dimethylolcyclohexane terephthalate, polyalkylene naphthalate (PAN) and polyhydroxy-benzoates, and also block polyether esters derived from polyethers with hydroxyl terminal groups; and also polyesters modified with polycarbonates or MBS.

18. Polycarbonates and polyester carbonates.

19. Mixtures (polyblends) of the afore-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and co-polymers, PA/HDPE, PA/PP, PA/PPO, PBT/PC/ABS or PBT/PET/PC. Preference may be given to compositions wherein the thermoplastic polymer is high-impact polystyrene (HIPS), expandable polystyrene (EPS), extruded polystyrene (XPS), polyphenylene ether (PPE), polyamide, polyester, polycarbonate (PC) or a polymer blend of the type ABS (acrylonitrile-butadiene-styrene) or PC/ABS (polycarbonate/acrylonitrile-butadiene-styrene) or PPE/HIPS (polyphenylene ether/high-impact polystyrene), especially a polyamide, polyester or a PPE/HIPS blend. Special preference may be given to polymer compositions that comprise a filler or a reinforcing agent, especially glass-fibre-reinforced polymers, e.g., glass-fibre-reinforced polyamide.

20. Natural polymers, for example cellulose, starch (amylose and amylopectin), ligno-cellulose, proteins silk, polyhydroxyalkanoates, polypeptides, polysacharides: Xanthan gum, B-Glucans, chitosan and natural rubbers.

21. Bio polymers, for example polycaprolactones, polylactides, poly(Lactide-co-Glycolide) Copolymers (PLGA), poly(glycolic acid) (PGA) and polydioxanone (PDS).

A preferred embodiment relates to flame retardant compositions, wherein the polymer substrate (b) consists of polystyrene, polystyrene copolymers, polyethylene, polypropylene or blends of polypropylene with polyolefins. Examples are blends of polypropylene with polyethylene selected from the group consisting of high density polyethylene (HDPE), high molecular weight high density polyethylene (HMW HDPE), ultra high molecular weight high density polyethylene (UHMW HDPE), medium density polyethylene (MDPE), low density polyethylene (LDPE), linear low density polyethylene (LLDPE), branched low density polyethylene (BLDPE) and ethylene-propylene-diene ter-polymers (EPDM) containing small proportions of diene.

Disclosed embodiments relate to a flame retardant composition, which comprises, in addition to the components (a) and (b), as defined above, (c) further additives selected from the group consisting of polymer stabilizers and additional non-halogenated flame-retardants, such as melamine containing flame retardants, phosphorus containing flame-retardants, further nitrogen containing flame-retardants other than melamine containing flame retardants, and inorganic flame-retardants.

Stabilizers are optionally halogen-free and selected from nitroxyl stabilizers, nitrone stabilizers, amine oxide stabilizers, benzofuranone stabilizers, phosphite and phosphonite stabilizers, quinone methide stabilizers and monoacrylate esters of 2,2'-alkylidenebisphenol stabilizers.

Additional flame retardants as of present component (c) are known components, items of commerce or can be obtained by known methods.

Representative melamine containing flame retardants are for example, melamine comprising compounds, wherein the melamine structure: 1,3,5-triazine-2,4,6-triamin (=cyanuric acid triamide) or condensates thereof are present. The definition applies to monomeric, oligomeric or polymeric compounds of melamine, condensates of melamine or condensates with of melamine and phosphoric thereof.

Preferred melamine comprising compounds are melamine cyanurate, melamine phosphate, dimelamine phosphate, melamine pyrophosphate, melamine polyphosphate, melamine phenyl phosphonate, melamine borate, melamine ammonium phosphate, melamine ammonium polyphosphate, melamine ammonium pyrophosphate, melem, melam or melon or polyphosphates of melem, melam or melon.

Representative phosphorus containing flame-retardants are for example: Organic metal phosphinates (Aluminium phosphinates, Exolit OP, Clariant), pentaerythritol phosphates, tetraphenyl resorcinol diphosphite (FYROLFLEX® RDP, Akzo Nobel), tetrakis(hydroxy-methyl)phosphonium sulphide, triphenyl phosphate, diethyl-N,N-bis(2-hydroxyethyl)-amino-methyl phosphonate, hydroxyalkyl esters of phosphorus acids and cyclic phosphonates (ADK STAB FP 600/800/2200, Adeka Corp), AFLAMMIT PCO 900/800/700, (Thor GmbH), ammonium polyphosphate (APP). (EXOLIT AP 766, Clariant) or (HOSTAFLAM® AP750, Clariant), resorcinol diphosphate oligomer (RDP), phosphazene flame-retardants, 9,10-dihydro-9-oxa-10-phosphaphenanthrene-10-oxide) (DOPO) or its derivatives, di(ethylenediamine) phosphate (DEDAP), and ethylenediamine diphosphate (EDAP) or their mixtures (e.g., BUDIT 3167, Budenheim).

Further nitrogen containing flame retardants other than melamine containing flame retardants are, for example, isocyanurate flame-retardants, such as polyisocyanurate, esters of isocyanuric acid or isocyanurates, melamine metal phosphates (SAFIRE® 200/400/600, Floridienne Chimie). Representative examples are hydroxyalkyl isocyanurates, such as tris-(2-hydroxyethyl)isocyanurate, tris(hydroxymethyl)isocyanurate, tris(3-hydroxy-n-proyl)isocyanurate or triglycidyl isocyanurate. Further examples are: benzoguanamine, tris(hydroxyethyl) isocyanurate, allantoin, glycouril, melamine cyanurate, urea cyanurate, poly-[2,4-(piperazine-1,4-yl)-6-(morpholine-4-yl)-1,3,5-triazine]/piperazin (MCA® PPM TRIAZINE HF, MCA Technologies) azoalkanes and related compounds (e.g.AZONOR, azine, azoxy, hydrazone, triazenyl, INAZO), NOR compounds (FLAMESTAB® NOR116, TINUVIN™ NOR 371, BASF), or ammonium polyphosphate. The sulfenamides can also be used together with synergists based on other radical generators e.g., disulfides or peroxides.

Representative organohalogen flame-retardants are, for example: Polybrominated diphenyl oxide (DE-60F, Great Lakes Corp.), decabromodiphenyl ethane (SAYTEX™ 8010, Albemarle), hexabromocyclododecane (SAYTEX™ HP 900P, Albemarle), brominated polymers and oligomers such as styrene-butadiene block copolymers (EMERALD INNOVATION™ 3000, Chemtura, GREEN ARMOR™, GREEN CREST™, Albemarle, FR-122P™, ICL), polyphenylene oxide and its derivatives, brominated polyacrylates (FR-1025 P™, ICL), decabromodiphenyl oxide (DBDPO; SAYTEX® 102E), tris[3-bromo-2,2-bis(bromomethyl)propyl] phosphate (PB 370®, FMC Corp.), tris(2,3-dibromopropyl)phosphate, tris(2,3-dichloropropyl)phosphate, chlorendic acid, tetrachlorophthalic acid, tetrabromophthalic acid, poly-β-chloroethyl triphosphonate mixture, tetrabromobisphenol A bis(2,3-dibromopropyl ether) (PE68), brominated epoxy resin, ethylene-bis(tetrabromophthalimide) (SAYTEX® BT-93), bis(hexachlorocyclopentadieno) cyclooctane (DECHLORANE PLUS®), chlorinated paraffins, octabromodiphenyl ether, hexa-chlorocyclopentadiene derivatives, 1,2-bis(tribromophenoxy)ethane (FF680), tetrabromo-bisphenol A (SAYTEX® RB 100), ethylene bis-(dibromonorbornanedicarboximide) (SAYTEX® BN-451), bis-(hexachlorocycloentadeno) cyclooctane, PTFE, tris-(2,3-dibromopropyl)-iso-cyanurate, and ethylene-bistetrabromophthalimide.

The flame-retardant mentioned above routinely combined with inorganic (hydr)oxide synergists. Most common for this use are aluminum (hydr)oxide, such as $Al(OH)_3$ or AlOOH, magnesium hydroxide, zinc or antimony oxides, e.g., $Sb_2O_3$ or $Sb_2O_5$. Boron compounds are suitable, too.

The above-mentioned additional flame retardant compounds are advantageously contained in the composition of disclosed embodiments in an amount from about 0.25% to about 45.0% by weight of the organic polymer substrate; for instance about 0.25% to about 35.0%; for example about 0.25% to about 30.0% by weight of the polymer.

As mentioned above, the composition according to disclosed embodiments may additionally contain one or more conventional additives, for example selected from pigments, dyes, plasticizers, anti-dripping agents such as fluorinated polymers (PTFE, Metablen A3800, Mitsubishi Rayon), nanoclays (Cloisite 30B) and borates (FIREBRAKE®, Borax), antioxidants, thixotropic agents, levelling assistants, basic co-stabilizers, metal passivators, metal oxides, organophosphorus compounds, further light stabilizers and mixtures thereof, especially pigments, phenolic antioxidants, calcium stearate, zinc stearate, UV absorbers of the 2-hydroxy-benzophenone, 2-(2'-hydroxyphenyl)benzotriazole and/or 2-(2-hydroxyphenyl)-1,3,5-triazine groups.

The additives mentioned above are optionally contained in an amount of 0.01 to 10.0%, especially 0.05 to 5.0%, relative to the weight of the polymer substrate b).

Disclosed embodiments accordingly relate also to the use of the compounds of formula (I) as defined above for imparting flame-resistant properties to a polymer substrate, for example synthetic polymers, especially to thermoplastics, and also to a method of imparting flame-resistant properties to synthetic polymers, wherein at least one compound of formula (I) according to disclosed embodiments is incorporated in the polymer substrate or is applied to their surface.

The incorporation of the compounds of formula (I) and the optional additional components, as defined above, into the polymer substrate is carried out by known methods such as dry blending in the form of a powder, or wet mixing in the form of solutions, dispersions or suspensions for example in an inert solvent, water or oil. The compound of formula (I) and optional further additives may be incorporated, for example, before or after molding or also by applying the dissolved or dispersed additive or additive mixture to the polymer material, with or without subsequent evaporation of the solvent or the suspension/dispersion agent. They may be added directly into the processing apparatus (e.g., extruders, internal mixers, etc.), e.g., as a dry mixture or powder, or as a solution or dispersion or suspension or melt.

Alternatively, the compound of disclosed embodiments can be incorporated to the backbone of a polymeric substrate or of part of a polymeric substrate, or of one or more polymeric component(s) of the polymeric substrate. Grafting can be effected in a manner known in the art using compounds of formula (I) which comprise functionalities in the substituents R1, R2, R3, R10, R30, R40 and/or R50 e.g., double or triple bond(s), OH, —$NH_2$, —COOH, which are reactive with the functionalities of the polymeric material. Thus the compounds of formula (I) and their use as flame retardants cover also such embodiments, wherein they are incorporated chemically to a part or all of the polymeric material ("functionalised/grafted" polymeric material) of the polymeric substrate.

If polymeric substrate comprises two or more different polymeric materials, the compound(s) of formula (I) can be combined by mixing or grafting with one of the materials, and the rest be added to the obtained first composition.

The addition of the additive components to the polymer substrate (b) can be carried out in all customary mixing machines in which the polymer is melted and mixed with the additives. Suitable machines are known to those skilled in the art. They are predominantly mixers, kneaders and extruders. If a plurality of components is added, these can be premixed or added individually. In such operations, the polymer can be used in the form of powder, granules, solutions, and suspensions or in the form of lattices.

The compounds of formula (I) (a) and optional further additives can also be added to the polymer substrate (b) in the form of a master batch ("concentrate") which contains the components in a concentration of, for example, about 1.0% to about 40.0% and optionally 2.0% to about 20.0% by weight incorporated in a polymer. In such operations, the polymer can be used in the form of powder, granules, solutions, and suspensions or in the form of lattices.

Incorporation can take place prior to or during the shaping operation. The materials containing the additives described herein may be optionally used for the production of molded articles, for example roto-molded articles, injection molded articles, profiles and the like, and especially a fiber, spun melt non-woven, film or foam. Thus, disclosed embodiments may pertain to molded or extruded articles, such as pipes, wire and cables, fibers, spun melt non-woven or a foam comprising the composition of disclosed embodiments.

Thus, in accordance with the disclosed embodiments, a compound of formula (I) as defined in herein and composition comprising compound of formula (I) as further defined herein can be used for providing a flame resistant products.

The compounds of formula (I) and the polymers comprising one or more repeating unit(s), wherein at least one of the repeating units comprises a sulfenamide moiety of formula (II) can be prepared by methods known by person skilled in the art or by methods demonstrated below for the synthesis of examples of compound of formula (I) of the disclosed embodiments. Suitable methods are described for example in Chemical Reviews, 1989, 89 (4), 689-712.

The polymer comprising one or more repeating units, wherein at least one of the repeating units comprises a sulfenamide moiety of formula (II) can be prepared e.g., by substituting amine groups (—NH) of one or more repeating units by —SR3. Alternatively, moieties of formula (II) can be linked to a polymeric backbone by suitable liking groups.

EXAMPLES

All chemicals used were of reagent grade and purchased from Aldrich. $^1$H and $^{13}$C NMR spectra were recorded on a Bruker Avance 600 ($^1$H 600.1 MHz, $^{13}$C 150.9 MHz). Sulfenyl chlorides were synthesized according to literature (Li, Yuye; Shi, Yi; Huang, Zhong-Xing; Wu, Xin-Hu; Xu, Peng-Fei; Wang, Jian-Bo; Zhang, Yan, Organic Letters (2011), 13(5), 1210-1213).

In the following, RT stands for room temperature, RH for room humidity.

Example 1

Synthesis of 2,2,6,6-tetramethyl-1-(phenylthio)piperidin-4-one

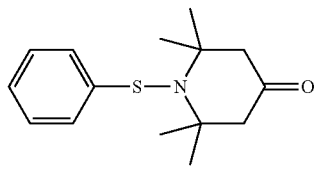 [SMILES: CC1(C)CC(=O)CC(C)(C)N1Sc1ccccc1]

A solution of benzenesulfenyl chloride (6.62 g, 46 mmol) in CCl$_4$ (50 mL) was added drop wise to a suspension of 2,2,6,6-tetramethylpiperidin-4-one (17.85 g, 115 mmol) in CCl$_4$ (50 mL) under argon at RT and stirred overnight. The reaction mixture was washed twice with 50 ml of H$_2$O, and the combined water phases were washed once with 25 ml of CH$_2$Cl$_2$. Organic phases were combined, dried over Na$_2$SO$_4$ and evaporated. Recrystallization and multiple washing in diethyl ether gave the pure product in 71% yield.

$^1$H NMR (600 MHz, CDCl3): δ 7.37 (dd, J=8.3, 3.1 Hz, 2H), 7.29 (ddd, J=8.3, 7.2, 3.1 Hz, 2H), 7.07 (td, J=7.2, 2.1 Hz, 1H), 2.80 (d, J=13 Hz, 2H), 2.43 (d, J=13 Hz, 2H), 1.37 (s, 6H), 1.29 (s, 6H)

$^{13}$C NMR (150 MHz, CDCl3): δ 208.2, 144.9, 128.4, 124.3, 121.6, 64.0, 55.2, 32.2, 26.9

Example 2

Synthesis of 1-((4-methoxyphenyl)thio)-2,2,6,6-tetramethylpiperidin-4-one

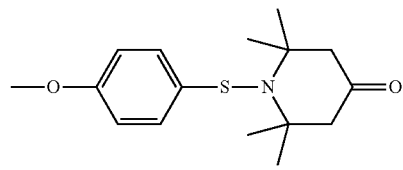 [SMILES: COc1ccc(SN2C(C)(C)CC(=O)CC2(C)C)cc1]

The same procedure as above was used but starting from the 4-methoxybenzenesulfenyl chloride (8.03 g, 46 mmol). Yield 73%.

1H NMR (600 MHz, CDCl$_3$): δ 7.27 (d, J=8.3 Hz, 2H), 6.87 (d, J=8.3 Hz, 2H), 3.79 (s, 3H), 2.78 (d, J=12.9 Hz, 2H), 2.42 (d, J=12.9 Hz, 2H), 1.38 (s, 6H), 1.29 (s, 6H)

$^{13}$C NMR (150 MHz, CDCl$_3$): 208.7, 157.5, 135.8, 123.8, 114.6, 64.4, 55.4, 32.8, 27.1

Example 3

Synthesis of 2,2,6,6-tetramethyl-1-((4-nitrophenyl)thio)piperidin-4-one

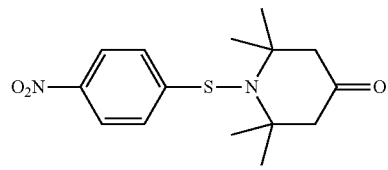 [SMILES: CC1(C)CC(=O)CC(C)(C)N1Sc1ccc([N+](=O)[O-])cc1]

The same procedure as above was used but starting from the 4-nitrobenzenesulfenyl chloride (8.74 g, 46 mmol). Yield 62%

$^1$H NMR (250 MHz, CDCl$_3$): δ 8.15 (d, J=8.3 Hz, 2H, CH), 7.49 (d, J=8.3 Hz, 2H, CH), 2.83 (d, J=12.9 Hz, 2H, CH$_2$), 2.46 (d, J=12.9 Hz, 2H, CH$_2$), 1.35 (s, 6H, CH$_3$), 1.31 (s, 6H, CH$_3$)

$^{13}$C NMR (63 MHz, CDCl$_3$): δ 207.2, 154.8, 144.9, 123.8, 121.8, 64.4, 54.8, 31.8, 26.8

Example 4

Synthesis of 1-(2-nitrophenylthio)-2,2,6,6-tetramethylpiperidin-4-one

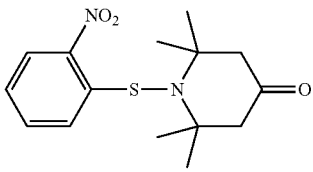 [SMILES: CC1(C)CC(=O)CC(C)(C)N1Sc1ccccc1[N+](=O)[O-]]

The same procedure as above was used but starting from the 4-nitrobenzenesulfenyl chloride (8.74 g, 46 mmol). Yield 17%

1H NMR (250 MHz, CDCl$_3$): δ 8.26 (d, J=8.3 Hz, 1H, CH), 8.19 (d, J=8.2 Hz, 1H, CH), 7.60 (t, J=7.6 Hz, 1H, CH), 7.23 (t, J=7.6 Hz, 1H, CH), 2.82 (d, J=12.7 Hz, 2H, CH$_2$), 2.45 (d, J=12.7 Hz, 2H, CH$_2$), 1.36 (s, 6H, CH$_3$), 1.29 (s, 6H, CH$_3$)

13C NMR (63 MHz, CDCl$_3$): δ 208.2, 146.9, 142.4, 133.4, 126.2, 125.8, 124.5, 63.9, 55.5, 31.2, 27.3

Example 5

Synthesis of 2,2,6,6-tetramethyl-1-(4-methylphenylthio)piperidin-4-one

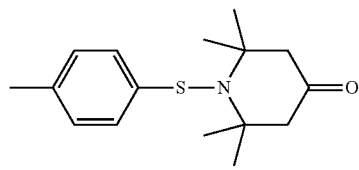 [SMILES: Cc1ccc(SN2C(C)(C)CC(=O)CC2(C)C)cc1]

The same procedure as above was used but starting from the 4-methylbenzenesulfenyl chloride (7.27 g, 46 mmol). Yield 28%

$^1$H NMR (250 MHz, CDCl$_3$): δ 7.24 (d, J=8.4 Hz, 2H, CH), 7.11 (d, J=8.4 Hz, 2H, CH), 2.80 (d, J=12.7 Hz, 2H, CH$_2$), 2.42 (d, J=12.7 Hz, 2H, CH$_2$), 2.31 (s, 3H, CH$_3$), 1.38 (s, 6H, CH$_3$), 1.28 (s, 6H, CH$_3$)

$^{13}$C NMR (63 MHz, CDCl$_3$): δ 208.3, 141.3, 133.9, 129.2, 121.8, 64.0, 55.1, 32.3, 26.7, 20.9

Example 6

Synthesis of 1-(2,4,6-trimethylphenylthio)-2,2,6,6-tetramethylpiperidin-4-one

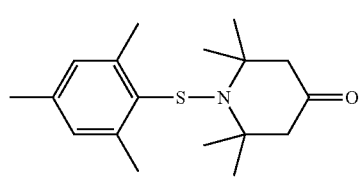 [SMILES: Cc1cc(C)c(SN2C(C)(C)CC(=O)CC2(C)C)c(C)c1]

The same procedure as above was used but starting from the 2,4,6-trimethylbenzenesulfenyl chloride (7.27 g, 46 mmol). Yield 53%

1H NMR (250 MHz, CDCl$_3$): δ 6.78 (s, 2H), 2.56 (s, 6H), 2.53 (s, 3H), 2.23 (s, 4H), 1.34 (s, 12H)

13C NMR (63 MHz, CDCl$_3$): δ 208.4, 136.2, 135.0, 130.4, 128.9, 64.8, 55.4, 55.2, 32.0, 21.4, 21.2

Example 7

Synthesis of 1-(2-pyridylthio)-2,2,6,6-tetramethylpiperidin-4-one

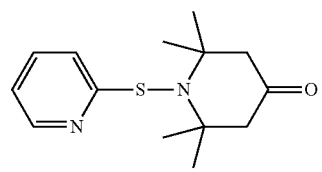 [SMILES: CC1(C)CC(=O)CC(C)(C)N1Sc1ccccn1]

The same procedure as above was used but starting from the 2-pyridylsulfenyl chloride (6.67 g, 46 mmol). Yield 40%

$^1$H NMR (250 MHz, CDCl$_3$): δ 8.37 (m, 1H, CH), 7.60 (m, 2H, CH), 6.95 (m, 1H, CH), 2.80 (d, J=13.1 Hz, 2H, CH$_2$), 2.45 (d, J=13.1 Hz, 2H, CH$_2$), 1.38 (s, 6H, CH$_3$), 1.31 (s, 6H, CH$_3$)

$^{13}$C NMR (63 MHz, CDCl$_3$): δ 208.0, 167.8, 148.7, 136.4, 119.0, 117.8, 64.0, 55.0, 31.9, 26.8

Example 8

Synthesis of 2,2,6,6-tetramethyl-1-(phenylthio)-4-piperidyl methacrylate

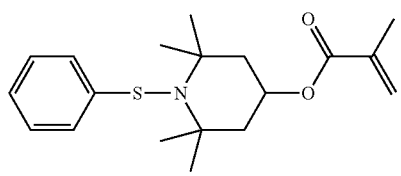 [SMILES: C=C(C)C(=O)OC1CC(C)(C)N(Sc2ccccc2)C(C)(C)C1]

The same procedure as above was used but starting from the benzenesulfenyl chloride (1.92 g, 13.36 mmol) and 2,2,6,6-tetramethyl-4-piperidyl methacrylate (7.5 g, 33.4 mmol). Yield 71%

The obtained product can be further polymerized to yield PMMA with pendant sulfenamide groups.

$^1$H NMR (250 MHz, CDCl$_3$): δ 7.51 (d, 2H), 7.32 (m, 2H), 7.07 (t, 1H), 6.15 (m, 1H), 5.61 (m, 1H), 5.27 (m, 1H), 2.12 (d, 2H), 1.99 (s, 3H), 1.80 (t, 2H), 1.40 (s, 6H), 1.33 (s, 6H)

$^{13}$C NMR (63 MHz, CDCl$_3$): δ 167.1, 145.5, 136.7, 128.3, 125.5, 123.9, 121.8, 67.1, 60.9, 45.7, 32.3, 25.8, 18.3

Example 9

Synthesis of disulfenylideneamino)sulfenyl-2' 2' 6' 6-tetramethylpiperidin-4-one

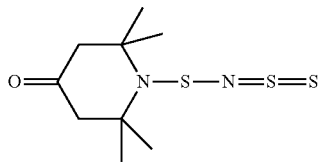

Into solution of 31.0 g (0.2 mol) of 2,2,6,6-tetramethylpiperidinone in 500 mL of toluene was added dropwise a solution of 27.0 g (0.2 mol) of sulfur monochloride in 80 mL of hexane with stirring at 10-15° C. over a period of 2 h. After the addition was completed, the reaction mixture was poured into 300 g of ice and 200 g of 35% aqueous ammonia. The organic phase was then separated, washed with water and dried over magnesium sulfate. Evaporation of the solvent under reduced pressure gave a red solid, which was chromatographed on Silica gel 60 with toluene to give red crude crystals in 14% yield.

$^1$H NMR (600 MHz, CDCl$_3$): δ 2.67 (s, 4H, CH$_2$), 1.46 (s, 12H, CH$_3$)

$^{13}$C NMR (150 MHz, CDCl$_3$): δ 206.7, 63.0, 54.2, 31.7

Example 10

Synthesis of 1,2-bis(2,2,6,6-tetramethyl-1-(phenylthio)piperidin-4-ylidene)hydrazine

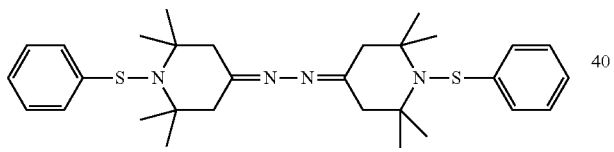

To a solution of hydrazine monohydrate (2.265 g, 45.2 mmol) in EtOH (375 mL) was added slowly 2,2,6,6-tetramethyl-1-(phenylthio)piperidin-4-one (25 g, 94.9 mmol) at 0° C. The mixture was heated over a steam bath for 15 min and then refluxed for 3 h. Reaction was let proceed for an additional 12 h at RT before saturated water solution of NaHCO$_3$ (150 mL) was added. The precipitate was filtered off, dissolved in CH$_2$Cl$_2$ and washed with water. The organic phase was dried over Na$_2$SO$_4$ and solvent was evaporated. Recrystallization from boiling EtOH or i-PROH gave pure product in 69% yield.

$^1$H NMR (600 MHz, CDCl3): δ 7.26 (d, J=8.3 Hz, 4H), 7.18 (dd, J=8.3, 7.3 Hz, 4H), 6.96 (td, J=7.3, 2.1 Hz, 2H), 3.38 (d, J=13.0 Hz, 1H), 3.17 (d, J=13.0 Hz, 1H), 2.59 (d, J=13.1 Hz, 1H), 2.55 (d, J=13.1 Hz, 1H), 2.46 (d, J=13.1 Hz, 2H), 2.23 (d, J=13.3 Hz, 1H), 2.17 (d, J=13.3 Hz, 1H), 1.3-1.26 (m, 12H), 1.23 (s, 3H), 1.19 (s, 3H), 1.14 (s, 3H), 1.13 (s, 3H)

$^{13}$C NMR (150 MHz, CDCl$_3$): δ 165.09, 162.64 (C=N), 145.56 (C—S), 128.45, 124.31, 122.09 (CH), 49.44, 49.26, 42.79, 42.68 (CH2), 32.15, 32.12, 32.06, 32.04, 26.89, 26.74, 26.28, 26.12 (CH3)

Example 11

Synthesis of trans-2,5-dimethyl-1,4-bis(phenylthio)piperazine

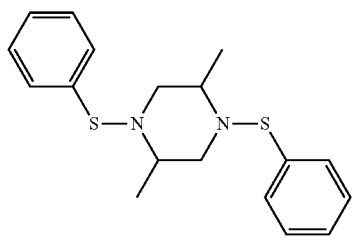 [SMILES: CC1CN(Sc2ccccc2)C(C)CN1Sc1ccccc1]

Trans-2,5-dimethyl piperazine (0.51 g, 3.5 mmol) was dissolved in 20 mL of CCl$_4$. Solution of benzenesulfenylchloride in CCl$_4$ (3.18 ml of 1.1 mM) was added drop wise during 1 h under argon at room temperature. White precipitate was formed. The reaction mixture was left to react for 12 h and washed twice with 10 mL of H$_2$O. Organic phases were combined, dried over MgSO$_4$ and evaporated. Recrystallization from diethyl ether gave the compound in 52% yield.

$^1$H NMR (600 MHz, CDCl$_3$): δ 7.38 (d, J=7.7 Hz, 4H), 7.32 (t, J=7.7 Hz, 4H) 7.22 (t, J=7.2 Hz, 2H), 3.24 (dd, J=11.9, 2.6 Hz, 2H), 2.96 (m, 2H), 2.81 (d, J=11.9 Hz, 2H)

$^{13}$C NMR (150 MHz, CDCl$_3$): δ 17.7, 57.8, 65.0, 127.0, 128.5, 128.8, 137.5

Example 12

Synthesis of 1-butylsulfanyl-2' 2' 6'6-tetramethylpiperidine

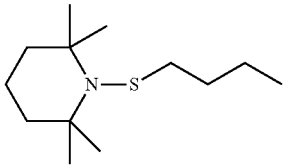

2,2,6,6-tetramethylpiperidine (17.7 g, 0.125 mol) in toluene (20 mL) was cooled to 0° C. and n-butylsulfenyl chloride (6.2 g. 0.05 mol) in toluene was added drop wise so the temperature did not exceed 10° C. The resulting yellow mixture was left to react overnight at RT. The solid particles were filtrated and the organic phase was extracted with diethyl ether and evaporated. Pure product was obtained as a yellow liquid, yield 70%.

$^1$H NMR (600 MHz, CDCl$_3$): δ 2.60 (t, J=7.0 Hz, 2H, CH$_2$), 1.53 (m, 4H, CH$_2$), 1.39 (m, 6H, CH$_3$), 1.26 (m, 6H, CH$_3$), 1.10 (m, 6H, CH$_3$), 0.87 (t, J=6.5 Hz, 3H, alkyl CH$_3$)

$^{13}$C NMR (150 MHz, CDCl$_3$): δ 59.1, 43.8, 40.9, 33.8, 28.7, 24.0, 22.4, 17.4, 13.9

Example 13

Synthesis of 4,4'-thiobis-morpholine

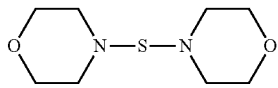 [SMILES: C1CN(SN2CCOCC2)CCO1]

A solution of bromine (1.47 g, 9.2 mmol) in CH$_2$Cl$_2$ (40 mL) was added slowly at 0° C. to a stirred suspension of sodium thiosulfate pentahydrate (1.14 g, 4.6 mmol), morpholine (3.0 g, 34.4 mmol) and hexane (50 mL). The reaction mixture was allowed to warm to room temperature, stirred for 12 h, filtered and organic solvent was removed under vacuum. Recrystallization from methanol gave pure product in 73% yield.

$^1$H NMR (250 MHz, CDCl$_3$): δ 3.63 (d, J=4.1 Hz, 2H, CH$_2$), 3.28 (d, J=4.1 Hz, 2H, CH$_2$)
$^{13}$C NMR (63 MHz, CDCl$_3$): δ 67.8, 57.7

Example 14

Synthesis of 1,1'-thiobis-(2,6-dimethyl)piperidine

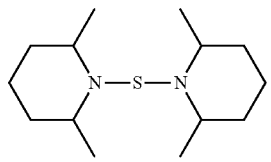 [SMILES: CC1CCCC(C)N1SN1C(C)CCCC1C]

To a solution of 2,6-dimethylpiperidine (5.0 g, 45.0 mmol) in anhydrous DMF (30 mL) was added sulfur monochloride (6.07 g, 45.0 mmol) in several portion at 28° C. The reaction mixture was stirred for 20 h at 28° C. and filtered. The filtrate is dissolved in CHCl$_3$ and washed with water. Organic solvent is evaporated to give the pure product in 60% yield.

$^1$H NMR (250 MHz, CDCl$_3$): δ 3.06 (m, 4H, CH), 1.86-1.62 (m, 12H, CH$_2$), 1.53 (s, 6H, CH$_3$), 1.50 (s, 6H, CH$_3$)
13C NMR (63 MHz, CDCl$_3$): δ 54.3, 30.3, 22.9, 19.5

Example 15

Synthesis of 1,1'-thiobis-(2,2,6,6-tetramethyl)piperidine

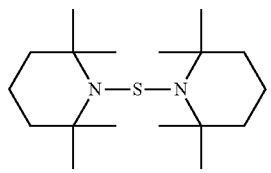 [SMILES: CC1(C)CCCC(C)(C)N1SN1C(C)(C)CCCC1(C)C]

The same procedure as above was used but starting from 2,2,6,6-tetramethylpiperidine (6.34 g, 45.0 mmol). Yield 55%

$^1$H NMR (250 MHz, CDCl$_3$): δ 1.69 (m, 12H, CH$_2$), 1.57 (s, 12H, CH$_3$), 1.56 (s, 12H, CH$_3$)
13C NMR (63 MHz, CDCl$_3$): δ 57.0, 35.2, 27.6, 16.4

Example 16

Synthesis of N-1,5,9-((4-methoxyphenyl)thio))-bis-(2,2,6,6-tetramethyl-4-piperidyl)-amine

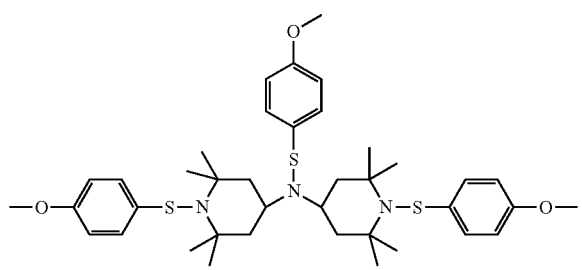

Under nitrogen atmosphere, a solution of 4-methoxybenzenesulfenylchloride (0.6 g, 3.4 mmol) in CCl$_4$ (50 mL) was added drop wise at 0° C. to a solution of bis(2,2,6,6-tetramethyl-4-piperidyl)-amine (prepared according to EP 0336895) (2.5 g, 8.5 mmol) and triethylamine (0.5 g, 5.1 mol) in CCl$_4$ (50 mL). The reaction mixture was stirred for 12 h at RT. The organic phase was washed with water and dried over sodium sulfate. Recrystallization in diethyl ether gave 0.45 g of a mixture of mono, di and tri-substituted derivatives.

Example 17

Synthesis of 1,1'-thiobis phtalimide

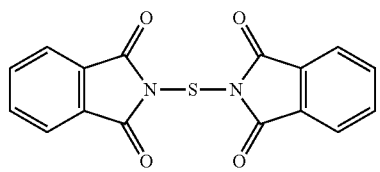 [SMILES: O=C1c2ccccc2C(=O)N1SN1C(=O)c2ccccc2C1=O]

The same procedure as in Example 10 was used but starting from phtalimide (6.61 g, 45.0 mmol). Yield 58%
$^1$H NMR (250 MHz, CDCl$_3$): δ 7.84 (m, 4H), 7.71 (m, 4H)
$^{13}$C NMR (63 MHz, CDCl$_3$): δ 166.1, 135.2, 131.3, 124.4

Example 18

Synthesis of 1,1'-thiobis-carbazole

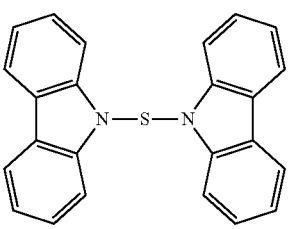 [SMILES: c1ccc2c(c1)c1ccccc1n2Sn1c2ccccc2c2ccccc21]

Sulfur powder (0.16 g, 2.5 mmol), carbazole, (6.68 g, 40 mmol) and pyridine (7 mL) were mixed under inert atmosphere and heated to 135° C. until dissolution of the reagents. A solution of iodine (1.27 g, 5 mmol) in pyridine (7 mL) was introduced to the reaction mixture and the mixture was stirred until decolorization. The solid was filtered, washed with water and dried under vacuum. The solid was washed with THF three times to yield 43% of the product.

$^{13}$C NMR (63 MHz, THF): δ 137.5, 127.4, 123.6, 121.5, 118.1, 108.7

Example 19

Synthesis of 2-[(4-methoxyphenyl)thio]-1H-Isoindole-1,3(2H)-dione

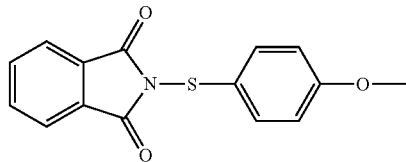 [SMILES: COc1ccc(SN2C(=O)c3ccccc3C2=O)cc1]

The synthesis was performed according to procedure disclosed in Gilis, H. Martin; Greene, Lana; Thompson, Alison, Synlett (2009), (1), 112-116.

Example 20

Synthesis of 9-(phenylthio)-9H-carbazole

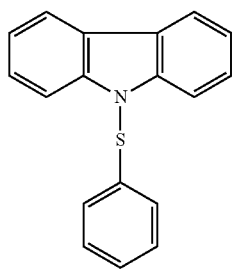 [SMILES: c1ccc(Sn2c3ccccc3c3ccccc32)cc1]

Under nitrogen atmosphere, a solution of benzenesulfenyl chloride (2.6 g, 17.9 mmol) in CCl$_4$ (50 mL) was added drop wise during 2 h at 0° C. to a solution of 9H-carbazole (3.0 g, 17.9 mmol) and triethylamine (2.73 g, 27.0 mmol) in CH$_2$Cl$_2$ (200 mL). Reaction mixture was stirred for 12 h at RT. The organic phase was washed with water and dried over sodium sulfate. Recrystallization from diethyl ether gave the pure product in 75% yield.

$^1$H NMR (250 MHz, CDCl$_3$): δ 8.13 (d, 2H, J=8.3 Hz), 7.80 (d, J=7.8 Hz, 2H), 7.52 (t, J=7.8 Hz, 2H), 7.37 (t, J=7.3 Hz 2H), 7.19 (m, 3H), 7.03 (d, 2H, J=7.7 Hz)

$^{13}$C NMR (63 MHz, CDCl$_3$): δ 143.4, 138.0, 129.2, 126.1, 126.6, 124.6, 124.0, 121.2, 120.3, 111.1

Example 21

Synthesis of 9-[(4-methoxyphenyl)thio]-9H-carbazole

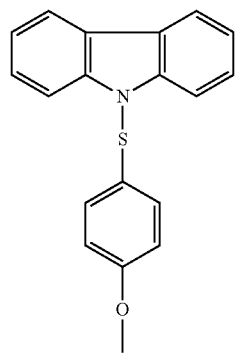 [SMILES: COc1ccc(Sn2c3ccccc3c3ccccc32)cc1]

Under nitrogen atmosphere, a solution of 4-methoxybenzenesulfenyl chloride (2.1 g, 12.0 mmol) in CCl$_4$ (50 mL) was added drop wise during 2 h at 0° C. to a solution of 9H-carbazole (2 g, 12.0 mmol) and triethylamine (1.8 g, 18.0 mol) in CH$_2$Cl$_2$ (160 mL). The reaction mixture was stirred for 12 h at RT. The organic phase was washed with water and dried over sodium sulfate. Recrystallization and multiple washing in diethyl ether gave 2.4 g of the pure product in 66% yield.

$^1$H NMR (250 MHz, CDCl$_3$): δ 8.08 (d, 2H, J=7.9 Hz), 7.91 (d, 2H, J=8.1 Hz), 7.55 (t, J=4.7 Hz, 2H), 7.34 (m, 4H), 6.76 (d, 2H, J=8.4 Hz), 3.66 (m, 3H)

$^{13}$C NMR (63 MHz, CDCl$_3$): δ 159.8, 143.5, 130.1, 128.0, 126.4, 124.6, 121.1, 120.2, 114.8, 111.2, 55.3

Example 22

Synthesis of N-2-naphthalenyl-N-phenyl-4-methyl-benzenesulfenamide

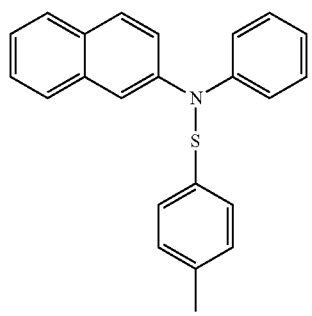 [SMILES: Cc1ccc(SN(c2ccccc2)c2ccc3ccccc3c2)cc1]

A solution of 4-methylphenylsulfenyl chloride (1.3 g, 8.1 mmol) in CCl$_4$ (50 mL) was added dropwise to a solution of N-phenyl-2-naphthalenamine (3.6 g, 16.2 mmol) and triethylamine (2.46 g, 24.4 mmol) in CH$_2$Cl$_2$ (50 mL). The mixture was stirred for 12 h at room temperature. The organic phase was washed with water and dried over sodium sulfate. Recrystallization and multiple washing in diethyl ether gave the pure product in 77% yield.

$^1$H NMR (250 MHz, CDCl$_3$): δ 8.41 (d, 1H, J=9.8 Hz), 7.81 (t, 2H, J=10.5 Hz), 7.63-7.04 (m, 13H), 2.29 (s, 3H)

$^{13}$C NMR (63 MHz, CDCl$_3$): δ 145.8, 141.4, 136.5, 135.2, 133.3, 131.3, 129.9, 129.5, 129.1, 128.5, 127.8, 126.5, 125.0, 123.0, 121.3, 118.8, 116.3, 108.5, 20.8

Example 23

Synthesis of N-bis[4-(1-methyl-1-phenylethyl)phenyl]-4-methylbenzenesulfenamide

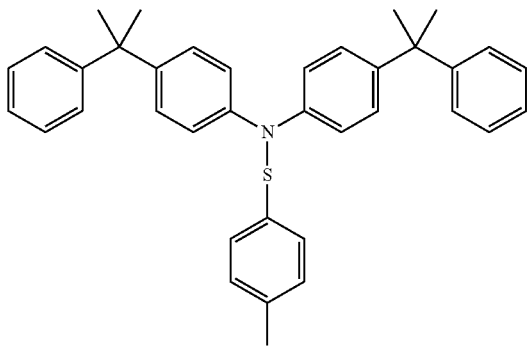 [SMILES: Cc1ccc(SN(c2ccc(C(C)(C)c3ccccc3)cc2)c2ccc(C(C)(C)c3ccccc3)cc2)cc1]

The same procedure as above was used but starting from 4-(1-methyl-1-phenylethyl)-N-[4-(1-methyl-1-phenylethyl)phenyl]-benzenamine (6.56 g, 16.2 mmol). Yield 40%

$^1$H NMR (250 MHz, CDCl$_3$): δ 7.36-7.15 (m, 22H, CH), 2.39 (s, 3H, CH$_3$), 1.76 (s, 12H, CH$_3$)

$^{13}$C NMR (63 MHz, CDCl$_3$): δ 150.5, 146.7, 145.7, 138.4, 135.4, 129.8, 128.0, 127.5, 126.9, 125.7, 123.1, 121.5, 42.5, 30.8, 21.1

Example 24

Synthesis of N-cyclohexyl-S-phenyl-N-(phenylthio)thiohydroxylamine

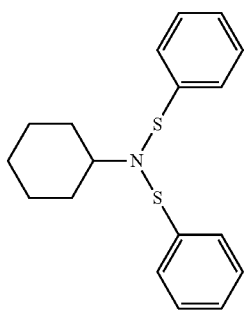 [SMILES: c1ccc(SN(Sc2ccccc2)C2CCCCC2)cc1]

The synthesis was performed according to procedure disclosed in Bowman, W. Russell; Clark, David N.; Marmon, Robert J. Journal of Chemical Research, Synopses (1995), (12), 514-15.

Example 25

Synthesis of 2,4,6-tris(4-morpholinylthio)-[1,3,5]-triazine

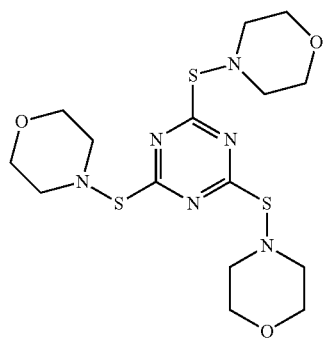 [SMILES: C1CN(Sc2nc(SN3CCOCC3)nc(SN3CCOCC3)n2)CCO1]

Trithiocyanuric acid (0.52 g, 3.0 mmol) and morpholine (0.86 g, 9.9 mmol) were added to a mixture of CuI (0.03 g, 0.15 mmol) and bipyridine (0.02 g, 0.15 mmol) in DMSO (20 mL). The reaction mixture was stirred at 100° C. for 24 h. The mixture was extracted with CH$_2$Cl$_2$ (25 mL) and washed twice with water (50 mL) and brine. The organic phase was dried over Na$_2$SO$_4$, filtered and organic solvent was evaporated to give the pure product in 89% yield.

1H NMR (250 MHz, CDCl$_3$): δ 3.77-3.67 (m, 24H)

13C NMR (63 MHz, CDCl$_3$): δ 165.3, 66.9, 43.6.

Example 33

Synthesis of bis(2,2,6,6-tetramethyl-1-(phenylthio)piperidin-4-yl)decanedioate

To a solution of Tinuvin® 770 (3.0 g, 6.24 mmol) and triethylamine (1.5 g, 15.0 mmol) in dry CH$_2$Cl$_2$ (15 mL) was added dropwise the solution of the benzenesulfenyl chloride (16 mL, 15.6 mmol) in CCl$_4$ during 1.5 h. After complete addition the reaction mixture was stirred for 12 h. The organic phase was washed with water and dried over sodium sulfate. Recrystallization from diethyl ether gave the pure product in 70% yield.

1H NMR (250 MHz, CDCl$_3$): δ 7.32-7.22 (m, CH, 8H), 7.03 (t, CH, 2H), 5.20 (m, CH, 2H), 2.32 (t, CH$_2$, 4H), 2.04 (m, CH$_2$, 4H), 1.72 (m, CH$_2$, 4H), 1.65 (m, CH$_2$, 4H), 1.33 (m, CH$_2$, 20H), 1.26 (s, CH$_3$, 12H)

13C NMR (63 MHz, CDCl$_3$): δ 173.7, 145.7, 128.3, 124.3, 122.0, 66.6, 60.9, 45.8, 34.6, 32.4, 29.0, 25.7, 24.6

Example 34

Synthesis of Bis(2,2,6,6-tetramethylpiperidin-4-yl)carbonate

Bis(2,2,6,6-tetramethylpiperidin-4-yl) carbonate was synthesized according to the procedure described in EP 1731 508 B1.

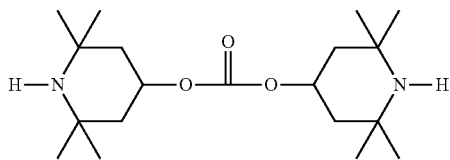

$^1$HNMR (CDCl$_3$): 5.04 (m, CH, 2H), 2.04 (d, CH$_2$, 2H), 2.02 (d, CH$_2$, 2H), 1.25 (s, CH$_3$, 12H), 1.20 (m, 4H), 1.17 (s, CH$_3$, 12H).

$^{13}$CNMR (CDCl$_3$): 154.28, 72.70, 51.76, 44.05, 35.01, 28.81.

Synthesis of bis(2,2,6,6-tetramethyl-1-(phenylthio) piperidin-4-yl) carbonate

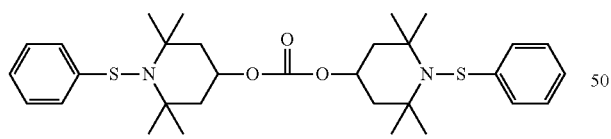

0.5 g, 0.0015 mol) was dissolved in dry dichloromethane (5 ml) and triethylamine (0.52 ml, 0.0036 mol) was added. Then, benzenesulfenyl chloride (4.07 mL, 0.0037 mol) was added dropwise. The reaction mixture was kept at RT overnight. The organic phase was washed with water (3*10 mL), dried over Na$_2$SO$_4$ and evaporated. The product was recrystallized twice from DEE and the title compound was obtained in 84% yield (0.7 g).

$^1$HNMR (CDCl$_3$): 7.24 (m, CH, 8H), 7.06 (t, CH, 2H), 5.04 (CH, 2H), 2.19, 2.16 (CH$_2$, 4H), 1.80 (CH$_2$, 4H), 1.36 (s, CH$_3$, 12H), 1.28 (s, CH$_3$, 12H).

13CNMR (CDCl$_3$): 154.21, 145.01, 128.03, 124.14, 121.67, 70.73, 61.18, 45, 27, 32.18, 25.46.

Example 35

Synthesis of 1,3-bis(phenylthio)-1H-benzo[d]imidazol-2(3H)-one

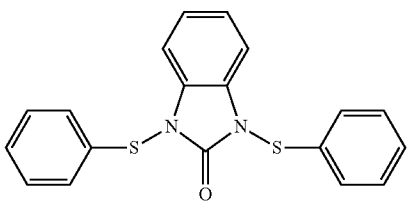 [SMILES: O=c1n(Sc2ccccc2)c2ccccc2n1Sc1ccccc1]

1,3-dihydro-2H-benzo[d]imidazol-2-one (2 g, 0.015 mol) was partly dissolved in the mixture (1:1) of dry dichloromethane (15 mL) and dry dimethylformamide (15 mL). The reaction was stirred for 10 min at RT and triethylamine was added (4.25 g, 0.042 mol). To this reaction mixture, a solution of dry benzenesulfenyl chloride (40.5 mL, 0.037 mol) was added dropwise over 1 h. The reaction mixture was stirred at RT for 12 h and dissolved in dichloromethane. The organic phase was washed three times with water, dried over sodium sulfate and evaporated. Recrystallization from diethyl ether gave the pure product in 52% yield.

$^1$HNMR (250 MHz, DMSO): δ 7.38 (4H), 7.35-7.33 (4H), 7.32-7.29 (4H), 7.19 (2H).
$^{13}$CNMR (250 MHz, DMSO): δ 156.4, 136.04, 131.92, 130.08, 128.71, 127.12, 124.18, 110.66.

Example 36

Synthesis of benzenesulfenyl Substituted Uvinul 5050 H

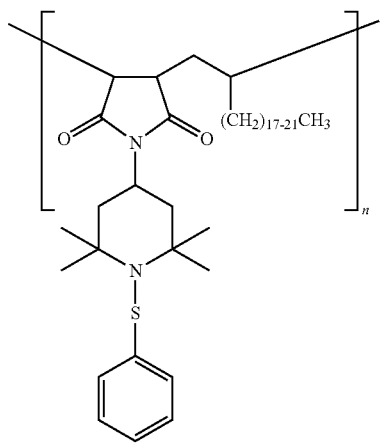

Uvinul® 5050 H (9.9 g, free amine calc. 18 mmol, molecular mass 3,000-4,000 g/mol) was dissolved in 150 mL of CH$_2$Cl$_2$ and triethylamine (45 mmol, 6.1 mL) was added. Benzenesulfenyl chloride solution (14.1 mL, 1.275 mmol/mL, 18 mmol) was added dropwise at RT under argon. Mixing was continued for 12 h, where after 50 mL of distilled water was added and the organic phase was separated. The CH$_2$Cl$_2$ solution was extracted three times with 40 mL of water, dried over Na$_2$SO$_4$, filtered, and the solvent was evaporated. The yellowish white solid polymeric product was obtained in 78% yield (9.2 g).

Commercially Available Compounds

Some commercially available sulfenamides and a sulfonamide were also tested, in addition to those prepared above, namely Compound 26
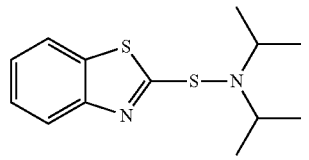

Compound 27
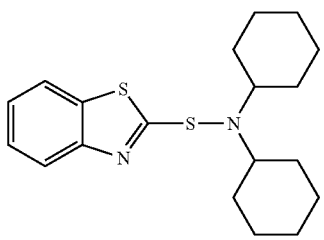

Compound 28
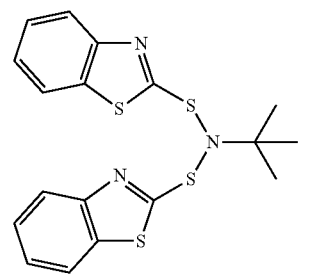

Compound 29
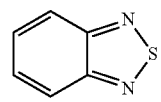

Compound 30
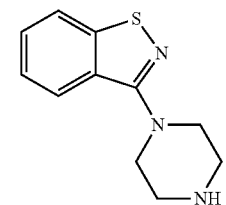

Compound 31
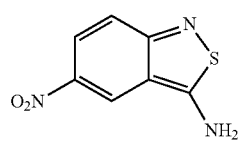

Compound 32
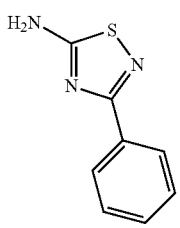

Reference compound A
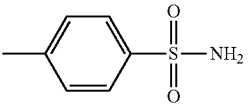

Test Example 1

Unless otherwise stated, commercial polypropylene or low density polyethylene and the compounds given in a table below, were blended in a Haake mixer (60 rpm, 5 min) at 210° C. and 190° C., respectively.

Test films (200 μm) were prepared by compression molding in a hot press. Pressing temperature was 210° C. for PP and 135° C. for LDPE.

The polystyrene samples were prepared by solvent casting from $CH_2Cl_2$. Films were dried at RT in vacuum oven, and conditioned for 3 days (23° C., 50% RH) prior to testing (thickness 400 μm).

The flame retardancy was investigated in accordance to DIN 4102-1 B2 (edge ignition, flame length=40 mm). The flame application time was 15 seconds.

In the following Tables: "Formulation" stands for the test sample's composition, wherein PP means polypropylene, LDPE means low density polyethylene and PS means polystyrene. The number of the flame retardant compound used is given as the number of the Example in which it was prepared above or as the number of commercially available compound as listed above. "Amount" refers to the amount of flame retardant compound added to the reference material. The average burning time is calculated from the application of flame. The overall result is given as Pass or Fail, according to the norm DIN 4102-1 B2. Low values of burning time and damage reflect increased flame retardancy.

Table 1 shows the test results for reference polypropylene (PP) (without any flame retardant) and for combinations of PP with various compounds as prepared in the examples above and some of commercially available compounds listed above. Table 2 similarly shows the test results for low density poly ethylene (LDPE) polymer and Table 3 for polystyrene (PS).

TABLE 1

Polypropylene (PP) LyondellBasell MOPLEN HP500N MFR (230° C./2.16 kg) = 12 g/10 min

| Formulation | Amount (wt %) | Average damage length (mm) | Average burning time (s) | DIN 4102-B2 (Pass/Fail) |
|---|---|---|---|---|
| Ref PP | 0 | 190 | 39 | Fail |
| Ref A | 1.0 | 180 | 76 | Fail |
| 1 | 0.5 | 71 | 15 | Pass |
| 2 | 0.5 | 56 | 8 | Pass |
| 3 | 1.0 | 80 | 10 | Pass |
| 4 | 1.0 | 76 | 13 | Pass |
| 5 | 0.5 | 68 | 9 | Pass |
| 7 | 1.0 | 64 | 16 | Pass |
| 10 | 0.5 | 78 | 15 | Pass |
| 10 | 1.0 | 102 | 12 | Pass |
| 12 | 0.5 | 90 | 22 | Pass |
| 13 | 1.0 | 77 | 21 | Pass |
| 15 | 1.0 | 126 | 19 | Pass |
| 16 | 0.5 | 94 | 31 | Pass |
| 19 | 1.0 | 69 | 18 | Pass |
| 20 | 1.0 | 75 | 12 | Pass |
| 21 | 1.0 | 61 | 7 | Pass |
| 22 | 0.8 | 110 | 18 | Pass |

TABLE 1-continued

Polypropylene (PP) LyondellBasell MOPLEN HP500N MFR
(230° C./2.16 kg) = 12 g/10 min

| Formulation | Amount (wt %) | Average damage length (mm) | Average burning time (s) | DIN 4102-B2 (Pass/Fail) |
|---|---|---|---|---|
| 23 | 0.6 | 82 | 20 | Pass |
| 24 | 1.0 | 69 | 14 | Pass |
| 26 | 0.5 | 93 | 27 | Pass |
| 27 | 0.5 | 98 | 23 | Pass |
| 28 | 0.5 | 74 | 14 | Pass |
| 33 | 1.0 | 81 | 10 | Pass |
| 34 | 1.0 | 76 | 11 | Pass |
| 35 | 0.5 | 67 | 14 | Pass |
| 36 | 1.0 | 80 | 12 | Pass |

TABLE 2

Low density polyethylene (LDPE) Borealis Polymers
CA7230, MFR (190° C./2.16 kg) 4.5 g/10 min

| Formulation | Amount (wt %) | Average damage length (mm) | Average burning time (s) | DIN 4102-B2 (Pass/Fail) |
|---|---|---|---|---|
| Ref LDPE | 0 | 190 | 37 | Fail |
| 1 | 0.5 | 108 | 30 | Pass |
| 10 | 0.5 | 133 | 36 | Pass |
| 10 | 1.0 | 122 | 28 | Pass |

TABLE 3

Polystyrene (PS)

| Formulation | Amount (wt %) | Average damage length (mm) | Average burning time (s) | DIN 4102-B2 (Pass/Fail) |
|---|---|---|---|---|
| Ref PS | 0 | 190 | n.d. | Fail |
| A | 1.0 | 190 | 70 | Fail |
| 28 | 2.0 | 107 | 29 | Pass |
| 28 | 3.5 | 94 | 16 | Pass | n.d. = not determined

Test Example 2

The flame retardant additives were blended with polystyrene (PS, Styrolution PS 158N) at 160° C., high impact polystyrene (HIPS, BASF polystyrol 454 KG2) at 170° C. or polypropylene (PP, Moplen HP500N) at 210° C. in a Haake mixer (60 rpm, 5 min) Test films (200 µm) were prepared by compression molding in a hot press. Pressing temperature was 210° C. for PP, 170° C. for HIPS and 160° C. for PS. The flame retardancy was investigated in accordance to DIN 4102-1 B2 standard (edge ignition, flame length=40 mm). The flame application time was 15 seconds. In addition, the flammability was tested according to UL 94 V standard. UL94 test bars were prepared by compression molding in a hot press (bar thickness 1.5 mm). Pressing temperature was 210° C. for PP and 160° C. for the PS. Total burning time was calculated for 4 sticks after the flame application ($t_1$ and $t_2$).

Polystyrene GPPS 25SPI (LG Chemical) was compounded by twin-screw extrusion with die temperature set at 200° C., followed by injection molding at 200° C. into 1.6 mm thick strips (127×12.7×1.6 mm³). Polypropylene Moplen HP 552R was compounded similarly with die temperature set at 210° C., followed by injection molding at 210° C. Total burning time was calculated for five specimens ($t_1$ and $t_2$).

Table 4 shows the flame retardant effect of sulfenamide 28 per. se. in two different polystyrene grades or its synergistic effect together with triphenylphosphate (TPP) in polystyrene PS 158N. It can be seen that very short burning time is observed for both PS grades containing only 5 wt % of the sulfenamide 28. PS 158N reached the UL 94 V2 classification (due to a burning drip), whereas GPPS 25SPI formulation reached the UL 94 V0 rating. In the case of PS 158N, the V0 can however also be obtained by using e.g., TPP and sulfenamide 28 as a synergistic combination.

Table 5 shows the synergistic effect of ammonium polyphosphate (APP) and aluminum trihydroxide (ATH) in polypropylene (PP). It can be seen that the flame retardant efficacy of APP and ATH can be significantly improved by addition of sulfenamide.

Table 6 shows the synergistic effect of sulfenamides with FP800 or FP600 in high impact polystyrene. It can be seen that no paper ignition took place when using the combination of sulfenamide with either FP800 or FP600, respectively.

Table 7 shows the strong synergistic effect between sulfenamide and PCO 900. It can be seen that the flame retardant performance of PCO 900 is strongly enhanced when adding sulfenamide to the polypropylene formulation, i.e., very short burning times.

Table 8 shows the synergistic effect of sulfenamide and Budit 3167 in polypropylene. It can be seen that the LOI value increased for Budit 3167 from 21 to 27 by adding 1 wt % of sulfenamide 33.

TABLE 4

Sulfenamide with triphenyphosphate (TPP, Disflamoll TP, Lanxess)
in polystyrene Styrolution PS 158N or GPPS 25SPI (LG Chemical)

| Formulation | Additive amount (wt %) | DIN 4102 B2 | | | UL 94 | |
|---|---|---|---|---|---|---|
| | | Average burning time (s)[1] | Rating | Paper ignition | Total burning time[2] (s) | Rating[3] |
| Ref PS | — | n.d. | Fail | Y | n.d. | NC |
| TPP | 20 | 90.8 | Pass | N | 15.9 | V2 |
| TPP | 5 | n.d. | n.d. | n.d. | >160 | NC |
| 28 | 5 | 19.2 | Pass | Y | 3.6 | V2 |
| TPP + 28 | 20 + 3.5 | 8.8 | Pass | N | 0.3 | V0 |
| TPP + 28 | 5 + 5 | 17.5 | Pass | N | 4.7 | 2 out of 4 samples reach V0 |
| 28[4] | 5 | n.d. | n.d. | n.d. | 4[5] | V0 | n.d. = not determined

[1]Calculated from the flame application

[2]Total burning time for 4 sticks after the flame application ($t_1$ and $t_2$)

[3]NC = non-classified, V-0 and V-2 according to UL 94 criteria

[4]Test lab ITRI United Kingdom. Polystyrene GPPS 25SPI (LG Chemical)

[5]Total burning time calculated for five specimens ($t_1$ and $t_2$).

TABLE 5

Synergistic effect with ammonium polyphosphate (APP) and aluminum trihydroxide (ATH) in polypropylene (PP)

| Formulation | Additive amount (wt %) | UL 94 Total burning time[1] (s) | Rating[2] |
|---|---|---|---|
| Reference, PP | — | n.d. | NC |
| APP | 30 | n.d. | NC |
| ATH | 30 | n.d. | NC |
| APP + 21 | 30 0.5 | 1.7 | V2 |
| ATH + 21 | 30 0.5 | 6.2 | V2 | n.d. = not determined
[1] Total burning time for 4 sticks after the flame application ($t_1$ and $t_2$)
[2] NC = non-classified, V-0 and V-2 according to UL 94 criteria

TABLE 6

High impact polystyrene (HIPS) polystyrol 454 C KG 2 from BASF (MVR 14 cm³/10 min) FP800 = ADK STAB FP-800 FP600 = ADK STAB FP-600

| Formulation | Additive amount (wt %) | Average damage length (mm) | Average burning time (s)[1] | DIN 4102 B2 | Paper ignition |
|---|---|---|---|---|---|
| HIPS | | 190 | n.d. | Fail | Y |
| 28 | 5 | 135 | 16.3 | Pass | Y |
| 28 | 10 | 127 | 11.6 | Pass | Y |
| FP800 | 20 | 164 | 35 | Fail | Y |
| FP800 + 28 | 20 + 5 | 126 | 10.2 | Pass | N |
| FP600 | 20 | 120 | 25.1 | Fail | Y |
| FP600 + 28 | 20 + 5 | 108 | 15.8 | Pass | N | n.d. = not determined
[1] Calculated from the flame application, film thickness 200 μm

TABLE 7

PP Moplen HP 552R (MFR 230° C./2.16 kg = 25 g/10 min), PCO 900 = Aflammit PCO 900 (Thor GmbH)

| Formulation | Additive amount (wt %) | DIN 4102 B2 Average damage length (mm) | Average burning time (s)[1] | DIN 4102 B2 | Paper Ignition | UL 94[2] Total burning time[3] (s) | Rating[4] | LOI |
|---|---|---|---|---|---|---|---|---|
| Ref, PP | | 158 | 60 | Fail | Y | 150+ | NC | 17 |
| PCO 900 | 8.0 | 86 | 18 | Pass | Y | 92+ | NC | 20 |
| PCO 900 | 4.0 | 81 | 26 | Pass | Y | 158+ | NC | 19 |
| PCO 900 + 20 | 8.0 + 1.0 | 97 | 6 | Pass | N | 3 | V2 | 24 |
| PCO 900 + 20 | 4.0 + 1.0 | 105 | 5 | Pass | N | 9 | V2 | 24 |

Calculated from the flame application, film thickness 200 µm

Test lab ITRI United Kingdom.

Total burning time calculated for five specimens.

NC=non-classified, V-2 according to UL 94 criteria.

TABLE 8

Synergistic effect of the sulfenamide 33 and Budit 3167 PP Moplen HP 552R (MFR 230° C./2.16 kg = 25 g/10 min)

| Formulation | Amount (wt %) | LOI (%) |
|---|---|---|
| Ref PP | 0 | 17 |
| Budit | 10 | 21 |
| 33 + Budit | 1 + 10 | 27 |

It will be obvious to a person skilled in the art that, as the technology advances, the inventive concept can be implemented in various ways. Disclosed embodiments are not limited to the examples described above but may vary within the scope of the claims.

The invention claimed is:

1. A composition comprising
    (a) one or more flame retardant compound(s) of formula (I), wherein the compound of formula (I) is selected from a group consisting of compounds of formula (Ia), (Ib), (Ic), (Id), (Ie), (If), (Ig), (Ih), and (Ii)

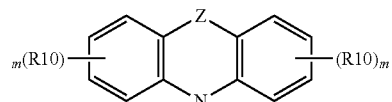
(Ia)

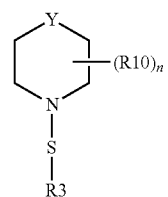
(Ib)

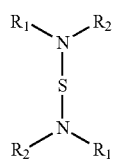
(Ic)

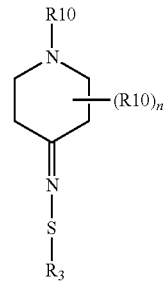
(Id)

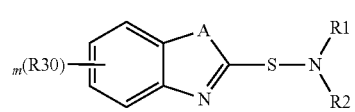
(Ie)

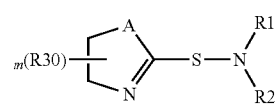
(If)

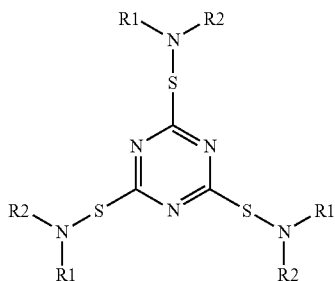
(Ig)

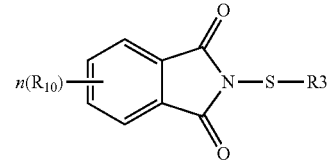
(Ih)

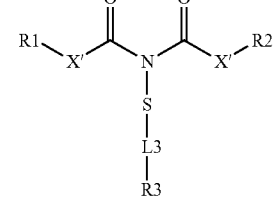
(Ii)

wherein

L3 is selected from a group consisting of a bond, $C_{1-10}$-alkylenyl, —(C=O)—, —O—(C=O)—, —(C=O)—O—, O, NH—(C=O)—, —(C=O)—NH—, NH, and NR20;

each R1 and R2 is independently selected from a group consisting of H, S(=O)$_p$R3, $C_{1-30}$-alkyl, $C_{3-7}$-cycloalkyl optionally substituted one or more times with R10, $C_{2-30}$-alkenyl, $C_{2-30}$-alkynyl, $C_{1-10}$-alkylenyl-X—$C_{1-20}$-alkyl, $C_{1-10}$-alkylenyl-X—$C_{1-7}$-cycloalkyl optionally substituted one or more times with R10, a saturated or partly unsaturated mono- or bicyclic heterocycle optionally substituted one or more times with R10, and a mono- or bicyclic aryl or heteroaryl optionally substituted one or more times with R10; or R1, and R2 together with the N atom they are attached to form a NR1R2 group selected from a group consisting of a saturated or partly unsaturated mono- or bicyclic heterocycle optionally substituted one or more times with R10; a mono-, bi-, tri-, tetra- or pentacyclic heteroaryl optionally substituted one or more times with R10; N=CR1'R2'; and N=S=S;

R3 is selected from a group consisting of $C_{1-30}$-alkyl, $C_{3-7}$-cycloalkyl optionally substituted one or more times with R30, $C_{2-30}$-alkenyl, $C_{2-30}$-alkynyl, NR1R2, a saturated or partly unsaturated mono- or bicyclic heterocycle optionally substituted one or more times with R30, and a mono-, bi-, or tricyclic aryl or heteroaryl optionally substituted one or more times with R30;

or

L3, R1, and R3 together with the N atom and the S atom they are attached to form a group selected from a mono-, bi-, or tricyclic heteroaryl optionally substituted one or more times with R40, and a saturated or partly unsaturated mono- or bicyclic heterocycle optionally substituted one or more times with R40; and R2 is as defined above;

or

L3, R1, R2, and R3 together with the S atom and the N atom to which they are attached to form a mono-, bi- or tricyclic heteroaryl optionally substituted one or more times with R50;

each R1' and R2' is independently R1 or R2, respectively, as defined above, or R1' and R2' form together with the C atom they are attached to a CR1'R2' group selected from a group consisting of a $C_{3-7}$-cycloalkyl optionally substituted one or more times with R10, a saturated or partly unsaturated mono- or bicyclic heterocycle optionally substituted one or more times with R10, a mono- or bicyclic aryl or heteroaryl optionally substituted one or more times with R10, each R10 is independently selected from a group consisting of $NO2$, CN, $SO_3H$, COOH, COOR20, CHO, COR20, OCOR20, O(C=O)O—(NR1"R2")-S(=O)$_p$R3, =O, =S, R20, NHCOR20, $NH_2$, NHR20, $N(R20)_2$, OH, OR20, $OSiH_3$, $OSi(R20)_3$, S(=O)$_p$R3, =N—S(=O)$_p$R3, —N=N—(R1"R2"N)—S(=O)$_p$R3, and =N—N=(R1"R2"N)—S(=O)$_p$R3, wherein R1"R2"N forms a monocyclic saturated heterocycle optionally substituted with one or more R10'; provided that when R10 is O(C=O)O—(NR1"R2")-S(=O)$_p$R3, S(=O)$_p$R3, =N—S(=O)$_p$R3, —N=N—(R1"R2"N)—S(=O)$_p$R3, or =N—N=(R1"R2"N)—S(=O)$_p$R3, the R3 is not substituted with NR1R2 or SNR1R2;

each R10' is independently selected from a group consisting of $NO_2$, CN, $SO_3H$, COOH, COOR20, CHO, COR20, OCOR20, =O, R20, NHCOR20, $NH_2$, NHR20, $N(R20)_2$, OH, OR20, $OSiH_3$, and $OSi(R20)_3$;

each R20 is independently selected from a group consisting of $C_{1-30}$-alkyl, $C_{2-30}$-alkenyl, $C_{2-30}$-alkynyl, aryl, $C_{1-10}$-alkylenyl-aryl, heteroaryl, and $C_{1-10}$-alkylenyl-heteroaryl, wherein the aryl or heteroaryl is optionally substituted one or more times with $C_{1-4}$-alkyl, $NO_2$, CN, $NH_2$, $NMe_2$, OH and/or OMe;

each R30 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, and S(=O)$_p$—NR1R2, provided that when R30 is NR1R2 or S(=O)$_p$—NR1R2 the NR1R2 is not substituted with O(C=O)O—(NR1"R2")-S(=O)$_p$R3, S(=O)$_p$R3, =N—S(=O)$_p$R3, —N=N—(R1"R2"N)—S(=O)$_p$R3, or =N—N=(R1"R2"N)—S(=O)$_p$R3;

each R40 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, S(=O)$_p$R3 and a saturated or partly unsaturated monocyclic heterocycle optionally substituted one or more times with R10', provided that when R40 is NR1R2 or S(=O)$_p$R3 the R3 is not substituted with NR1R2 or S(=O)$_p$—NR1R2 and the NR1R2 is not substituted with O(C=O)O—(NR1"R2")-S(=O)$_p$R3, —S(=O)$_p$R3, =N—S(=O)$_p$R3, —N=N—(R1"R2"N)—S(=O)$_p$R3, or =N—N=(R1"R2"N)—S(=O)$_p$R3;

each R50 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, S(=O)$_p$R3, and a saturated or partly unsaturated monocyclic heterocycle optionally substituted one or more times with R10', provided that when R50 is NR1R2 or S(=O)$_p$R3 the R3 is not substituted with NR1R2 or S(=O)$_p$—NR1R2 and the NR1R2 is not substituted with O(C=O)O—(NR1"R2")-S(=O)$_p$R3, S(=O)$_p$R3, =N—S(=O)$_p$R3, —N=N—(R1"R2"N)—S(=O)$_p$R3, or =N—N=(R1"R2"N)—S(=O)$_p$R3; and each p is independently selected from the group consisting of 0, 1 and 2;

each m is independently 0, 1, 2, 3, or 4, n is from 0 to 8,

X' is a bond, N or O, Z is selected from a group consisting of a bond, O, S, NH, NR20, N—SR3, $CH_2$, CHR20, $C(R20)_2$, and C=O, A is S, O or NH, and Y is selected from the group consisting of a bond, $CH_2$, CHR10, $C(R10)_2$, N—SR3, C=O, C=N—SR3, and C=N—N(R1"R2"N)—SR3, (b) a polymeric substrate, wherein the composition is free of a halogenated flame retardant, and and R1, R2, R3, R10, R20, R30, R40 and R50 are as defined above.

2. The composition of claim 1, wherein the compound of formula (I) is incorporated chemically to a part or all of the polymeric substrate.

3. The composition of claim 1, which comprises, in addition to the components (a) and (b), (c) an additive selected from the group consisting of polymer stabilizers and additional flame-retardants, melamine containing flame retardants, phosphorus containing flame-retardants, nitrogen containing flame-retardants other than melamine containing flame retardants, and inorganic flame-retardants, wherein the additional flame retardant is a non-halogenated flame retardant.

4. The composition of claim 1, wherein

L3 is selected from a group consisting of a bond, $C_{1-10}$-alkylenyl, —(C=O)—, O, NH, and NR20;

each R1 and R2 is independently selected from a group consisting of H, S(=O)$_p$R3, $C_{1-30}$-alkyl, $C_{3-7}$-cycloalkyl optionally substituted one or more times with R10, $C_{2-30}$-alkenyl, $C_{2-30}$-alkynyl, $C_{1-10}$-alkylenyl-X—$C_{1-20}$-alkyl, $C_{1-10}$-alkylenyl-X—$C_{1-7}$-cycloalkyl optionally substituted one or more times with R10, a saturated or partly unsaturated mono- or bicyclic heterocycle optionally substituted one or more times with R10, and a mono- or bicyclic aryl or heteroaryl optionally substituted one or more times with R10; or R1 and R2 together with the N atom they are attached to form a NR1R2 group selected from a group consisting of a saturated or partly unsaturated mono- or bicyclic heterocycle optionally substituted one or more times with R10, a mono-, bi-, tri-, tetra- or pentacyclic heteroaryl optionally substituted one or more times with R10; N=CR1'R2'; and N=S=S;

R3 is selected from a group consisting of $C_{1-30}$-alkyl, $C_{3-7}$-cycloalkyl optionally substituted one or more times with R30, $C_{2-30}$-alkenyl, $C_{2-30}$-alkynyl, NR1R2, a saturated or partly unsaturated mono- or bicyclic heterocycle optionally substituted one or more times with R30, and a mono-, bi-, or tricyclic aryl or heteroaryl optionally substituted one or more times with R30;

or

L3, R1, and R3 together with the N atom and the S atom they are attached to from a group selected from a mono-, bi-, or tricyclic heteroaryl optionally substituted one or more times with R40, and a saturated or partly unsaturated mono- or bicyclic heterocycle optionally substituted one or more times with R40; and R2 is as defined above;

or

L3, R1, R2, and R3 together with the S atom and the N atom to which they are attached to form a mono,- bi- or tricyclic heteroaryl optionally substituted one or more times with R50;

each R1' and R2' is independently R1 or R2, respectively, as defined above, or R1' and R2' form together with the C atom they are attached to a CR1'R2' group selected from a group consisting of a $C_{3-7}$-cycloalkyl optionally substituted one or more times with R10, a saturated or partly unsaturated mono- or bicyclic heterocycle optionally substituted one or more times with R10, a mono- or bicyclic aryl or heteroaryl optionally substituted one or more times with R10, X is O, S, NH, NR20, P, Si, or Se;

each R10 is independently selected from a group consisting of $NO_2$, CN, $SO_3H$, COOH, COOR20, CHO, COR20, OCOR20, =O, R20, NHCOR20, $NH_2$, NHR20, $N(R20)_2$, OH, OR20, $OSiH_3$, $OSi(R20)_3$, $S(=O)_pR3$, =N—$S(=O)_pR3$, —N=N—(R1"R2"N)—$S(=O)_pR3$, and =N—N=(R1"R2"N)—$S(=O)_pR3$, wherein R1"R2"N forms a monocyclic saturated heterocycle optionally substituted with one or more R10'; provided that when R10 is $S(=O)_pR3$, =N—$S(=O)_pR3$, —N=N—(R1"R2"N)—$S(=O)_pR3$, or =N—N=(R1"R2"N)—$S(=O)_pR3$, said R3 is not substituted with NR1R2 or SNR1R2;

each R10' is independently selected from a group consisting of $NO_2$, CN, $SO_3H$, COOH, COOR20, CHO, COR20, OCOR20, =O, R20, NHCOR20, $NH_2$, NHR20, $N(R20)_2$, OH, OR20, $OSiH_3$, and $OSi(R20)_3$;

each R20 is independently selected from a group consisting of $C_{1-30}$-alkyl, $C_{2-30}$-alkenyl, $C_{2-30}$-alkynyl, aryl, $C_{1-10}$-alkylenyl-aryl, heteroaryl, and $C_{1-10}$-alkylenyl-heteroaryl, wherein said aryl or heteroaryl is optionally substituted one or more times with $C_{1-4}$-alkyl, $NO_2$, CN, $NH_2$, $NMe_2$, OH and/or OMe;

each R30 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, and $S(=O)_p$—NR1R2, provided that when R30 is NR1R2 or $S(=O)_p$—NR1R2 said NR1R2 is not substituted with $S(=O)_p$R3, =N—$S(=O)_pR3$, —N=N—(R1"R2"N)—$S(=O)_pR3$, or =N—N=(R1"R2"N)—$S(=O)_pR3$;

each R40 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, $S(=O)_pR3$ and a saturated or partly unsaturated monocyclic heterocycle optionally substituted one or more times with R10', provided that when R40 is NR1R2 or $S(=O)_pR3$ said R3 is not substituted with NR1R2 or $S(=O)_p$—NR1R2 and said NR1R2 is not substituted with —$S(=O)_pR3$, =N—$S(=O)_pR3$, —N=N—(R1"R2"N)—$S(=O)_pR3$, or =N—N=(R1"R2"N)—$S(=O)_pR3$;

each R50 is independently selected from a group consisting of $NO_2$, CN, $SO_3H$, COOH, COOR20, CHO, COR20, OCOR20, =O, R20, OH, OR20, $OSiH_3$, $OSi(R20)_3$, NHCOR20, NR1R2, $S(=O)_pR3$, and a saturated or partly unsaturated monocyclic heterocycle optionally substituted one or more times with R10', provided that when R50 is NR1R2 or $S(=O)_pR3$ said R3 is not substituted with NR1R2 or $S(=O)_p$—NR1R2 and said NR1R2 is not substituted with $S(=O)_pR3$, =N—$S(=O)_pR3$, —N=N—(R1"R2"N)—$S(=O)_pR3$, or =N—N=(R1"R2"N)— $S(=O)_pR3$; and each p is independently selected from the group consisting of 0, 1 and 2.

5. The composition of claim 1, wherein compound of formula (I) is a compound of formula (Ia),

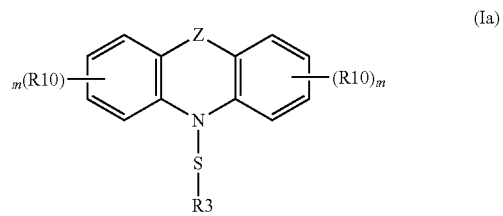

(Ia)

6. The composition of claim 1, wherein the compound of formula (I) is a compound of formula (Ib),

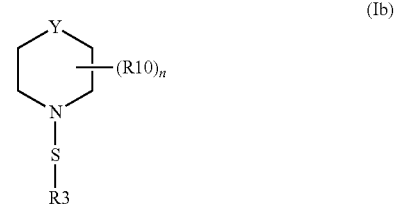

(Ib)

wherein n is from 0 to 8, Y is selected from a group consisting of $CH_2$, CHR10, $C(R10)_2$, N—SR3, C=O, C=N—SR3, and C=N—N(R1"R2"N)—SR3, wherein R1"R2"N forms a monocyclic saturated heterocycle.

7. The composition of claim 1, wherein the compound of formula (I) is a compound of formula (Ic)

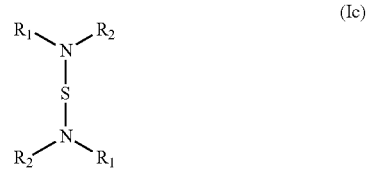

(Ic)

8. The composition of claim 1, wherein compound of formula (I) is a compound of formula (Ie)

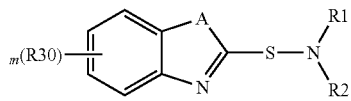
(Ie)

9. The composition of claim 1, wherein compound of formula (I) is a compound of formula (If)

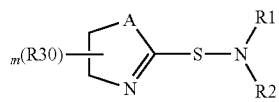
(If)

10. The composition of claim 1, wherein compound of formula (I) is a compound of formula (Ig),

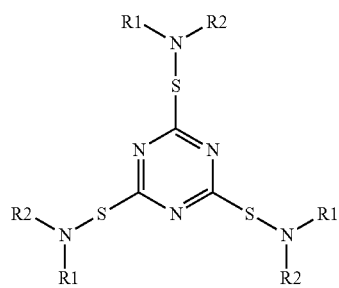
(Ig)

11. The composition of claim 1, wherein compound of formula (I) is a compound of formula (Ih)

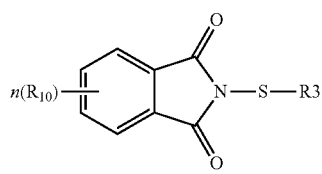
(Ih)

wherein n is 0 to 4.

12. The composition of claim 1, wherein compound of formula (I) is a compound of formula (Iac)

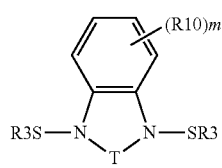
(Iac)

wherein m is 0, 1, 2 3, or 4 and T is selected from the group consisting of C=O, C=S, C=N—SR3, N—SR3, N, S, O and P.

13. The composition of claim 1, wherein compound of formula (I) is a compound of formula (Ibd)

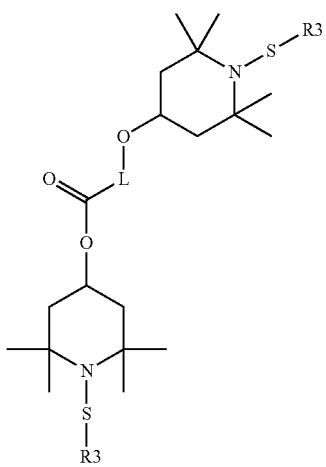
(Ibd)

wherein L is bond or $C_{1-10}$-alkylenyl-(C=O)—.

14. The composition of claim 1, wherein NR1R2 forms a group selected from:

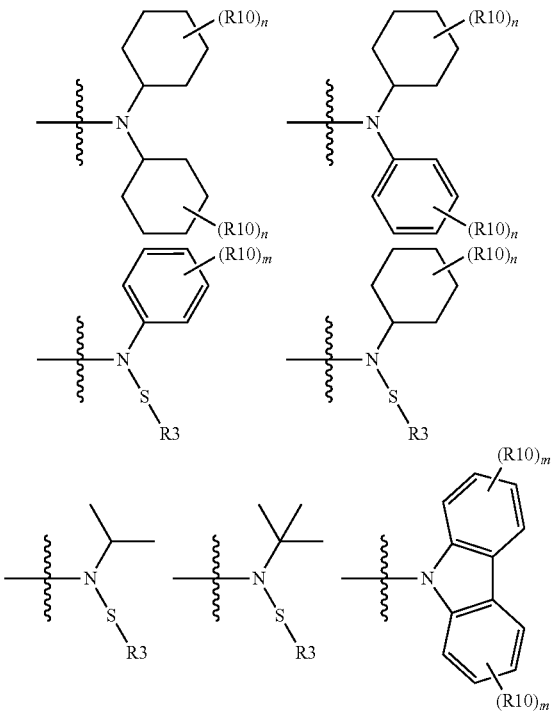

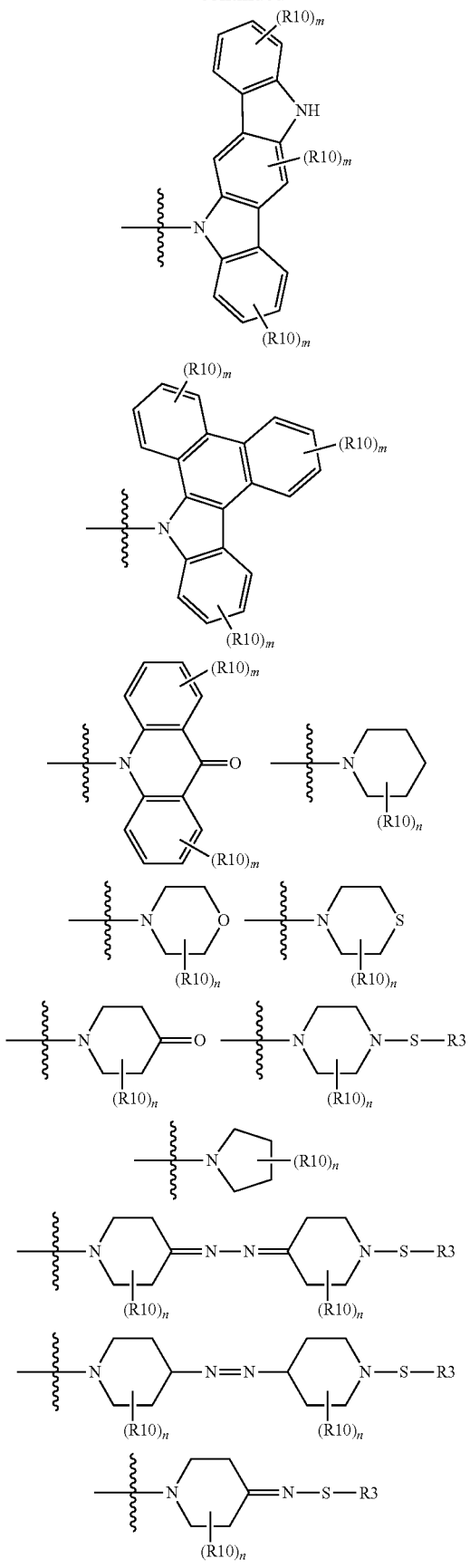

wherein each m is independently 0, 1, 2, 3, or 4, each n is independently 0, 1, 2, 3, 4, 5, 6, 7, or 8, and each R3, R10 and R20 independently.

15. The composition of claim 1, wherein R3 is a mono- bi- or tricyclic aryl or heteroaryl, optionally substituted one or more times with R30.

16. The composition of claim 1, wherein the compound of formula (I) is selected from the group consisting of:
2,2,6,6-tetramethyl-1-(phenylthio)piperidin-4-one (1);
1-((4-methoxyphenyl)thio)-2,2,6,6-tetramethylpiperidin-4-one (2);
2,2,6,6-tetramethyl-1-((4-nitrophenyl)thio)piperidin-4-one (3);
1-(2-nitrophenylthio)-2,2,6,6-tetramethylpiperidin-4-one (4);
2,2,6,6-tetramethyl-1-(4-methylphenylthio)piperidin-4-one (5);
1-(2,4,6-trimethylphenylthio)-2,2,6,6-tetramethylpiperidin-4-one (6);
1-(2-pyridylthio)-2,2,6,6-tetramethylpiperidin-4-one (7);
1,2-bis(2,2,6,6-tetramethyl-1-(phenylthio)piperidin-4-ylidene)hydrazine (8);
2,2,6,6-tetramethyl-1-(phenylthio)-4-piperidyl methacrylate (9);
1-[(1-disulfenylideneamino)sulfenyl-2'2'6'6-tetramethylpiperidin-4-one (10);
trans-2,5-dimethyl-1,4-bis(phenylthio)piperazine (11);
1-butylsulfanyl-2'2'6'6-tetramethylpiperidine (12);
4'-thiobis-morpholine (13);
1,1'-thiobis-(2,6-dimethyl)piperidine (14);
1,1'-thiobis-(2,2,6,6-tetramethyl)piperidine (15);
N-1,5,9-((4-methoxyphenyl)thio))-bis-(2,2,6,6-tetramethyl-4-piperidyl)amine (16);
1,1'-thiobis phtalimide (17);
1,1'-thiobis-carbazole (18);
2-[(4-methoxyphenyl)thio]-1H-Isoindole-1,3(2H)-dione (19);
9-(phenylthio)-9H-carbazole (20),
9-[(4-methoxyphenyl)thio]-9H-carbazole (21);
N-2-naphthalenyl-N-phenyl-4-methylbenzenesulfenamide (22);
N-bis[4-(1-methyl-1-phenylethyl)phenyl]-4-methylbenzenesulfenamide (23);
N-cyclohexyl-S-phenyl-N-(phenylthio)thiohydroxylamine (24);
2,4,6-tris(4-morpholinylthio)-[1,3,5]-triazine (25);
S-(benzo[d]thiazol-2-yl)-N,N-diisopropylthiohydroxylamine (26);

S-(benzo[d]thiazol-2-yl)-N,N-dicyclohexylthiohydroxylamine (27);
S-(benzo[d]thiazol-2-yl)-N-(benzo[d]thiazol-2-ylthio)-N-(tert-butyl)thiohydroxylamine (28);
benzo[c][1,2,5]thiadiazole (29);
3-(piperazin-1-yl)benzo[d]isothiazole (30);
5-nitrobenzo[c]isothiazol-3-amine (31); and
3-phenyl-1,2,4-thiadiazol-5-amine (32)
bis(2,2,6,6-tetramethyl-1-(phenylthio)piperidin-4-yl)decanedioate (33);
bis(2,2,6,6-tetramethyl-1-(phenylthio)piperidin-4-yl) carbonate (34); and
1,3-bis(phenylthio)-1H-benzo[d]imidazol-2(3H)-one (35).

17. The composition of claim 1, wherein the compound of formula (I) provides flame retarding properties to the polymeric substrate.

* * * * *